US008835392B2

(12) United States Patent
Schmidt et al.

(10) Patent No.: US 8,835,392 B2
(45) Date of Patent: Sep. 16, 2014

(54) MIMETIC PEPTIDES AND THE USE THEREOF IN THE FORM OF 20S, 26S AND IMMUNOPROTEASOME INHIBITORS

(75) Inventors: Boris Schmidt, Darmstadt (DE); Sumaira Umbreen, Darmstadt (DE); Hannes Braun, Hofheim (DE); Peter-Michael Kloetzel, Berlin (DE); Ulrike Kuckelkorn, Berlin (DE)

(73) Assignees: Technische Universität, Darmstadt (DE); Charité—Universitätsmedizin Berlin, Berlin (DE)

( * ) Notice: Subject to any disclaimer, the term of this patent is extended or adjusted under 35 U.S.C. 154(b) by 1366 days.

(21) Appl. No.: 11/817,628

(22) PCT Filed: Mar. 3, 2006

(86) PCT No.: PCT/EP2006/001975
§ 371 (c)(1),
(2), (4) Date: Sep. 23, 2008

(87) PCT Pub. No.: WO2006/092326
PCT Pub. Date: Sep. 8, 2006

(65) Prior Publication Data
US 2009/0012007 A1   Jan. 8, 2009

(30) Foreign Application Priority Data
Mar. 3, 2005   (DE) .......................... 10 2005 009 784

(51) Int. Cl.
*A61K 38/00*   (2006.01)
*A61P 43/00*   (2006.01)
*C07K 5/083*   (2006.01)
*C07K 5/062*   (2006.01)

(52) U.S. Cl.
CPC .............. *C07K 5/0808* (2013.01); *A61K 38/00* (2013.01); *C07K 5/06043* (2013.01)
USPC ....................................................... 514/18.9

(58) Field of Classification Search
CPC .. A61K 38/00; C07K 5/06043; C07K 5/0808; G06Q 10/06395
See application file for complete search history.

(56) References Cited

U.S. PATENT DOCUMENTS 5,693,617 A * 12/1997 Stein et al. .................. 514/20.1

FOREIGN PATENT DOCUMENTS

| EP | 1454627 | 9/2004 |
|---|---|---|
| JP | 61103897 | 5/1986 |
| WO | WO 9524914 | 9/1995 |
| WO | WO 9525533 | 9/1995 |
| WO | WO 0035868 | 6/2000 |
| WO | WO 2004089423 | 10/2004 |
| WO | WO 2006021413 | 3/2006 |

OTHER PUBLICATIONS

Sorg et al. "Progress in the preparation of peptide aldehydes via polymer supported IBX oxidation and scavenging by threonyl resin." Journal of Peptide Science 11: 142-152 (2005). Published online Sep. 24, 2004 in Wiley InterScience.*
Ando et al. "Z-Leu-Leu-Leu-H, a Neurite Outgrowth Factor Selectively Reacts with Lys-55 of 5-100β in a Possible Form of Schiff Base." The journal of Tokyo Academy of Health Science 3(2), 118-121, Sep. 25, 2000.*
Boillot, F., et al. "The Perseus Exobiology mission on MIR: behaviour of amino acids and peptides in Earth orbit." *Origins of Life and Evolution of the Biosphere: The Journal of the International Society for the Study of the Origin of Life*, Aug. 2002, pp. 359-385, vol. 32, No. 4.
Iqbal, M., et al. "Subsite requirements for peptide aldehyde inhibitors of human calpain I" *Bioorganic & Medicinal Chemistry Letters*, Mar. 4, 1997, pp. 539-544, vol. 7, No.5.
Saito, Y., et al. "The structure-function relationship between peptide aldehyde derivatives on initiation of neurite outgrowth in PC12h cells." *Neuroscience Letters*, Nov. 27, 1990, pp. 1-4, vol. 120, No. 1.
Saito, Y., et al. "Isolation and characterization of possible target proteins responsible for neurite outgrowth induced by a tripeptide aldehyde in PC12H cells." *Biochemical and Biophysical Research Communications* Apr. 15, 1992, pp. 419-426, vol. 184, No. 1.
Sorg, G., et al. "Progress in the preparation of peptide aldehydes via polymer supported IBX oxidation and scavenging by threonyl resin." *Journal of Peptide Science: An official Publication of the European Peptide Society*, Mar. 2005, pp. 142-152, vol. 11, No. 3.
Taguchi, T., et al. "Inhibition of DNA polymerases by tripeptide derivative protease inhibitors." *Biochemical and Biophysical Reseasrch Communications*, Jun. 30, 1992, pp. 1133-1140, vol. 185, No. 3.

* cited by examiner

*Primary Examiner* — Thomas Heard
(74) *Attorney, Agent, or Firm* — Saliwanchik, Lloyd & Eisenschenk

(57) ABSTRACT

The present invention relates to peptide-mimetic compounds, the synthesis and use thereof fort he inhibition of proteasomes and the induction of apoptosis in tumor cells. The present invention furthermore relates to pharmaceutical compositions comprising the compounds and the use of the compounds for a treatment of diseases, in particular cancer and neurodegenerative diseases.

14 Claims, 9 Drawing Sheets

MIMETIC PEPTIDES AND THE USE THEREOF IN THE FORM OF 20S, 26S AND IMMUNOPROTEASOME INHIBITORS

This application is a National Stage Application of International Application Number PCT/EP2006/001975, filed Mar. 3, 2006; which claims priority to German Application No. 102005009784.7, filed Mar. 3, 2005.

DESCRIPTION OF THE INVENTION

The present invention relates to peptide-mimetic compounds, the synthesis and use thereof fort he inhibition of proteasomes and the induction of apoptosis in tumour cells. The present invention furthermore relates to pharmaceutical compositions comprising the compounds and the use of the compounds for a treatment of diseases, in particular cancer and neurodegenerative diseases.

BACKGROUND OF THE INVENTION

The balance between the synthesis and the degradation processes of proteins is essential for the maintenance of the cellular homeostasis. Cells have two main metabolic pathways of protein degradation. A large number of the proteins is either digested by proteolytic enzymes in lysosomes or via the ubiquitin-proteasome-system. An imbalance between the protein synthesis and the degradation processes of proteins leads to a series of pathological processes (1).

The 26S proteasomes are protease-complexes that are composed of multiple subunits, perform the ATP-dependent degradation of poly-ubiquitinylated proteins. They are responsible for the majority of the non-lysosomal proteolysis in eukaryotic cells. They consist of the proteolytic 20S proteasome-core particles and carry a lid on one or both ends that is formed out of the regulatory 19S cap-particles (2, 3). The 20S core particle is a cylindrical assembly of 28 subunits that are arranged in 4 stapled heptamer-rings. 2 rings are formed by 7 subunits of the α-type and 2 rings by 7 subunits of the β-type (4, 5). Both inner β-rings form the central area of the cylinder and carry the proteolytic centres. In contrast to the prokaryotic 20S proteasomes that consist of 14 identical alpha and 14 identical proteolytically active subunits of the β-type, eukaryotic 20S proteasomes have only 3 proteolytically active subunits per β-ring. Proteasomes belong to the family of the N-terminal nucleophilic hydrolases (6, 7). A stimulation of mammalian cells with γ-interferon causes the exchange of the 3 active β-subunits β1, β2 and β5 by the immune homologues β1i, β2i, and β5i, leading to the formation of the immunproteasomes, which generate modified cleavage pattern of substrate peptides. It was shown that the functional integrity of the proteasome is essential for a multitude of cellular functions, such as, for example, the metabolic adaptation, cellular differentiation, cell cycle-control, stress response, the degradation of abnormal proteins and the generation of epitopes that are presented through MHC class I-receptors (for a review: see (8, 9)). Proteasomes are an important but not exclusive producer of the antigenic peptides (10, 11).

The dysregulation of the metabolic pathway of the ubiquitin-proteasome-protein degradation causes several diseases in the human, such as, for example, cancer, neurodegenerative, autoimmune- and metabolic diseases. The inhibition of the proteasomes influences the stability of many proteins, such as those that are involved in the regulation of the cell cycle. Thus, selective inhibitors of the multicatalytic proteasomal subunits are attractive targets in the development of drugs (12).

Most of the cells that are treated with proteasomal inhibitors are sensitized for the apoptosis (13, 14). Interestingly, tumour cells are usually are more sensitive against proteasomal inhibition than normal cells. Healthy cells are subject to an arrest of the cell cycle when treated with proteasomal inhibitors, but, nevertheless, in contrast to tumour cells are less prone for apoptosis (15, 16).

Until today, different proteasomal inhibitors were characterised (see FIG. 1). A distinction is made between selective inhibitors (4 lactacystin, 5 TMC-95A, 6 epoxomicin) and non-selective inhibitors (1 dichlorovinylester, 3 MG132) (17).

The most important proteasomal inhibitor is compound 2, also Bortezomib® or VELCADE™ (see FIG. 1). Bortezomib® was registered by the U.S. Food and Drug Administration (FDA) as drug only available on prescription for the treatment of multiple myeloma (18-20).

Another important proteasomal inhibitor is MG132 (compound 3 in FIG. 1). A decisive disadvantage of MG132 is its lack of/low selectivity in the inhibition of proteasomes (1, 17, 22, 38).

Furthermore, WO 96/13266 describes peptidic boric acid and -ester-compounds that are suitable as inhibitors of the proteasomal function.

The proteasomal amide hydrolysis differs from the amide hydrolysis of all other classes of proteases. Thereby, the particular features are the N-terminal threoninees. The mechanism is depicted in FIG. 2. When analysing the crystal structure of the 20S proteasome, it was revealed that Thr1O$^\gamma$ functions as the nucleophile, and the N-terminal amino group as the acyl-carrier (6). Covalent inhibitors can bind in the active centre, and in particular either via the hydroxyl group of the Thr1O$^\gamma$ or simultaneously via the free N-terminus and the Thr1O$^\gamma$ (for a review: see 17).

Effective in vivo inhibitors of the 20S proteasome thus require a high selectivity and at the same time a good ability to penetrate the cellular membranes. Furthermore, they can be characterized in that they covalently bind to the N-terminal threonine.

It is therefore the object of the present invention, to develop improved inhibitors of the proteasome that are characterized in particular by their selectivity to the proteasome as well as their irreversibility, and that are able to penetrate cellular membranes.

According to the invention, this object is solved by providing compounds having the formula

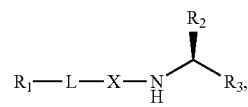

wherein $R_1$ to $R_5$ and X are selected independently from one another, and wherein $R_1$ is Boc, Z, Ac or H,
Z is benzyloxycarbonyl,
L is Leu,
X is Leu or Asp(OR$_4$),
$R_2$ is $CH_2$—$CH(CH_3)_2$,
$R_3$ is $CH_2$—OH, CH=O, CH(OH)—C≡C-phenyl, CH(OH)—C(O)—NH—$R_5$ or C(O)—C(O)—NH—$R_5$,
$R_4$ is t-butyl, benzyl or H,
$R_5$ is benzyl, 3-picolyl or phenyl,
and pharmaceutically acceptable salts thereof.
Excluded shall be a compound wherein, if X is Leu, $R_3$ is CH=O, preferably wherein, if X is Leu, $R_2$ is $CH_2$—CH (CH$_3$)$_2$ and R$_3$ is CH=O, particularly preferred wherein, if R$_1$ is Z and X is Leu, R$_2$ is CH$_2$—CH(CH$_3$)$_2$ and R$_3$ is CH=O.

In a preferred embodiment thereof, the invention comprises compounds, wherein
R$_1$ is Boc or Z,
L is Leu,
X is Asp(OR$_4$),
R$_2$ is CH$_2$—CH(CH$_3$)$_2$,
R$_3$ is CH$_2$—OH,
R$_4$ is t-butyl.

In a further preferred embodiment thereof, the invention comprises compounds, wherein
R$_1$ is Boc, Z or Ac,
L is Leu,
X is Asp(OR$_4$),
R$_2$ is CH$_2$—CH(CH$_3$)$_2$,
R$_3$ is CH=O,
R$_4$ is t-butyl or benzyl.

In a further preferred embodiment thereof, the invention comprises compounds, wherein
R$_1$ is Z,
L is Leu,
X is Leu,
R$_2$ is CH$_2$—CH(CH$_3$)$_2$,
R$_3$ is C(O)—C(O)—NH—R$_5$,
R$_5$ is benzyl, 3-picolyl or phenyl.

In a further preferred embodiment thereof, the invention comprises compounds, wherein
R$_1$ is Z,
L is Leu,
X is Leu,
R$_2$ is CH$_2$—CH(CH$_3$)$_2$,
R$_3$ is CH(OH)—C(O)—NH—R$_5$,
R$_5$ is phenyl.

In a further preferred embodiment thereof, the invention comprises compounds, wherein
R$_1$ is Z,
L is Leu,
X is Leu,
R$_2$ is CH$_2$—CH(CH$_3$)$_2$,
R$_3$ is CH(OH)—C≡C-phenyl.

Furthermore, compounds are comprised, wherein
R$_1$ is Z,
L is Leu,
X is Leu,
R$_2$ is CH$_2$—CH(CH$_3$)$_2$, phenyl or benzyl
R$_3$ is CH$_2$—O—C(Cl)=C—Cl.

The invention furthermore provides methods for producing a compound according to the invention. One such method preferably comprises a step of oxidation or reduction. Preferably, the method is characterized in that the oxidation takes place by using hypervalent iodine reagents.

Thereby, the method according to the invention preferably comprises the conversion of amino alcohols into peptide-mimetics (7-12) with a subsequent oxidation into peptide aldehydes (13-18), e.g. by hypervalent iodine reagents. The synthesis is also possible by reducing derivatized amino acid esters into the respective peptide aldehydes.

The synthesis of the compounds 7-18 according to the invention which started from compound 3 (MG132) as a lead-structure, was performed based on the established substrate-preferences of β-secretase (23) by means of standard methods. The synthesis is depicted in scheme I (see also example 1). The condensation of commercially available, protected dipeptides and amino acids with commercially available amino alcohols was followed by the oxidation into the aldehydes by IBX in DMSO (scheme I).

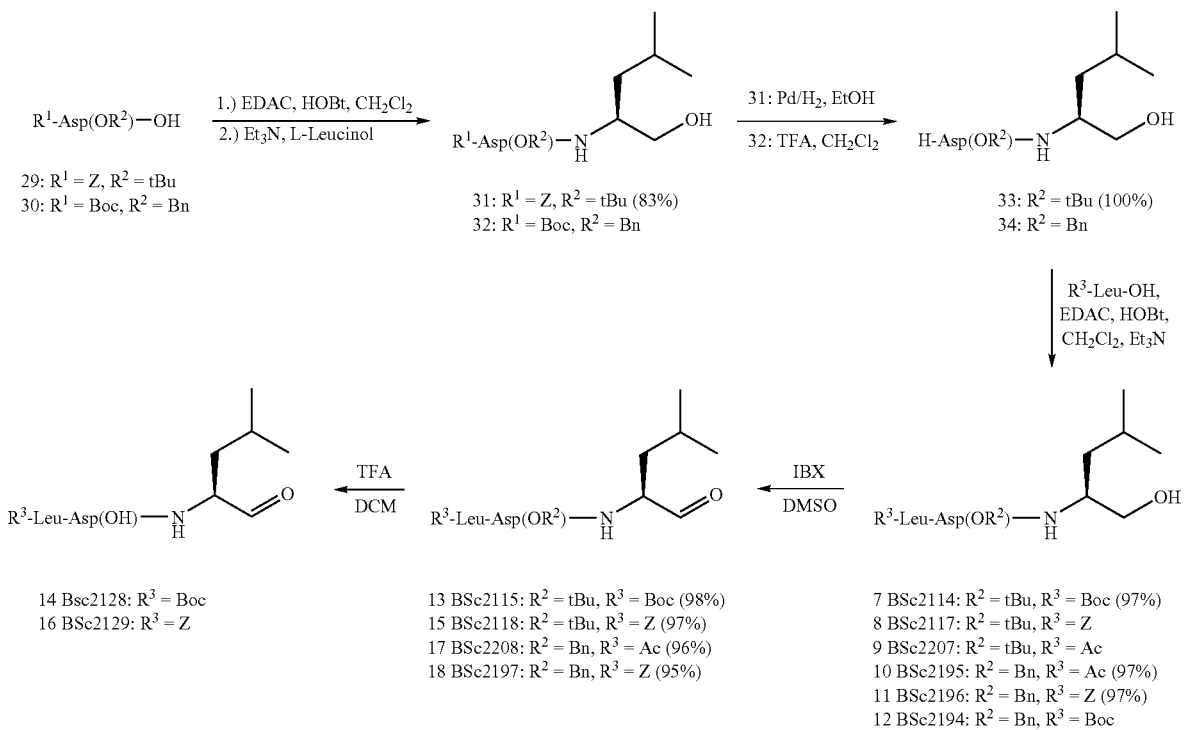

Scheme I (synthesis of the tripeptide-mimetics)

The intermediate, i.e. the alcohol-derivates 7-12, and the tripeptide aldehydes 13-18 were tested for their ability to inhibit the enzyme. The inhibition of the β-secretase was rather slightly pronounced (IC$_{50}$>200 μM, results not shown), nevertheless, several compounds were found as potent inhibitors of the 20S proteasome.

In general, peptide aldehydes exhibited no selectivity in the inhibition of enzymes. Thus, different groups were tested for their ability to inhibit threonine-proteases.

The non-selective dichlorovinylester 1 (see FIG. 1), which readily reacts with all possible nucleophiles, such as, for example, cysteine, serine and finally also threonine, served as a further lead-structure for the syntheses of compounds according to the invention. In addition, the aim was pursued to reduce the inherent over-activation of this compound. The "removal" of the acyl group of 1 could reduce the non-specific hydrolysis through ubiquitary nucleophiles, and results in quite stable dichlorovinylethers (28). The resulting ethers, the compounds according to the invention 19-20 (for the synthesis see scheme II and example 1), tolerate an acidic environment, but are hydrolysed readily at pH 11 and converted into α-chloroacetates, which, in turn, react with nucleophiles. This dual reactivity which is provided in a cascade-like reaction, corresponds to the specific requirements for an N-terminal threonine-protease-inhibitor.

Scheme II
(synthesis of dichlorovinylether 19 (BSc2158 and 20 (BSc2166))

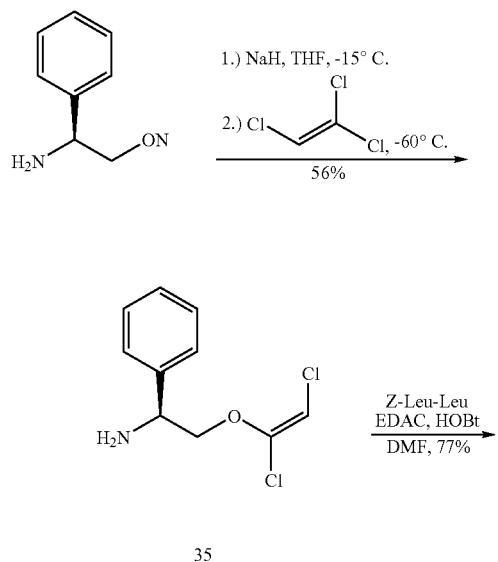

35

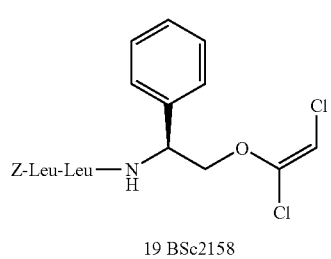

19 BSc2158

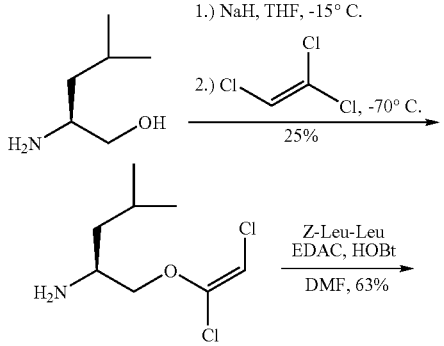

36

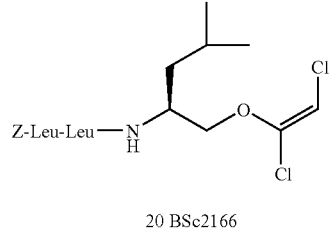

20 BSc2166

An analogous dual reactivity can be observed in propargyl-ketones. A similar compound was synthesized, but unfortunately the alcohol 21 (scheme III) withstood the oxidation into the desired ketone.

Scheme III
(addition of phenylacetylene to the aldehyde 3 (MG132))

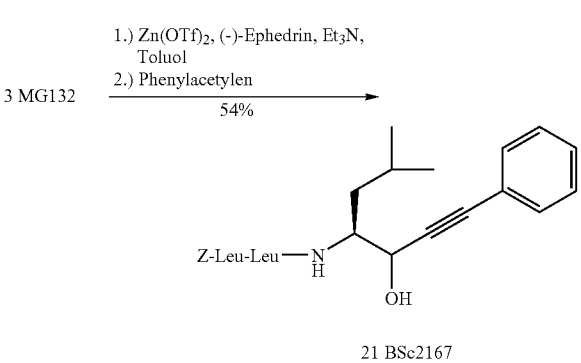

21 BSc2167

Thus, the further focus was laid on transition-state-mimetics and inhibitors. Lead-structures, such as statines (38), α-ketoamides, and chloromethyl ketones are well established in the inhibition of proteases. The combination of these structures with a β-selective tripeptide lead to the compounds 22-28 according to the invention (structures of 22-28, see FIG. 3). Compound 22 was prepared from commercial Z-Leu-Leu and chloromethyl leucine (scheme IV and example 1).

Scheme IV
(synthesis of the α-chloromethyl ketone 22 (BSc2160))

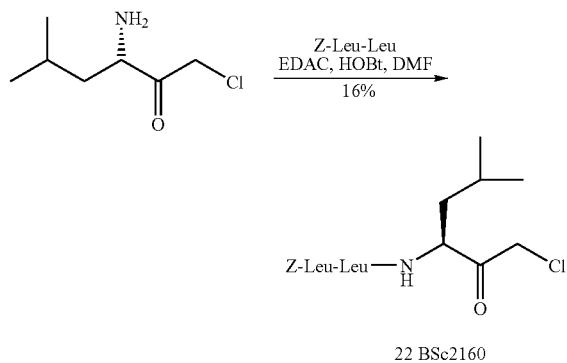

22 BSc2160

The compounds according to the invention 23-25 were obtained through a Passerini-reaction of MG132 (3) with three isonitriles. The subsequent oxidation through IBX in DMSO delivered the α-ketoamides 26-28 (scheme V and example 1).

Scheme V
Passerini-reaction with subsequent oxidation to the α-ketoamides

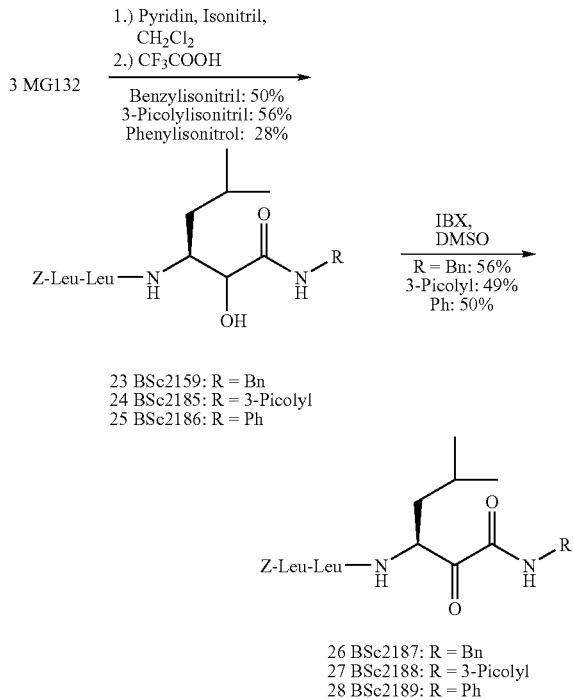

23 BSc2159: R = Bn
24 BSc2185: R = 3-Picolyl
25 BSc2186: R = Ph

26 BSc2187: R = Bn
27 BSc2188: R = 3-Picolyl
28 BSc2189: R = Ph

Proteasomes are involved in a series of different cellular processes. They are important for the control of the cellular cycle and protect cells against apoptosis by maintaining the balance of anti-apoptotic and pro-apoptotic proteins (9, 31, 32). The interest in potent and specific inhibitors that can be used as potential agents against cancer or neoplastic growth, is very high.

The present invention reports on the synthesis of inhibitors that are based on the proteasomal peptide-inhibitor MG132, which is a potent, but non-specific inhibitor. Side-chain modifications of this tripeptide should lead to a higher potency, selectivity and position-specific inhibition of the 20S proteasome. This assumption is based on a series of known and potent peptidic inhibitors (17, 33, 34, 35).

All compounds according to the invention were tested in cell-lysates for their inhibitory capacity. Thus, during the tests with the mimetics as synthesized, the serine-, cysteine- and metal-proteases were blocked with the protease-inhibitor-cocktail complete (Roche). The proteolysis of the hydrophobic substrate Suc-LLVY-AMC was reduced by 10 of the compounds according to the invention as examined (see also example 5, FIG. 4).

The specific inhibition of a single catalytic site is of specific interest for the development of drugs. Thus, the inhibition of the different proteasomal activities of the proteasome was analysed (see also example 6). The different cleavage-preferences of the proteasome were determined by the specific substrate for the hydrophobic (chymotrypsin-like), the trypsine-like and the caspase-like activities of isolated proteasomes. 12 of 22 derivatives according to the invention inhibited proteasomal activities with $IC_{50}$-values below 10 μM (see table 1). The peptidic derivatives 13 and 15 inhibited all of the proteasomal hydrolytic activities, whereas four compounds (18, 25, 26 and 27) inhibited the chymotryptic and the caspase-like sites.

Nevertheless, one additional aim of this analysis was the identification of completely selective inhibitors of the proteasomal activity. The tripeptidic alcohol 7 (and compound 8 with lower potency) specifically reduced the trypsine-like activity, and the compounds 16, 21, 22 and 28 resulted in an exclusive reduction of the chymotryptic activity. Notably the most potent of the new inhibitors have $IC_{50}$-values of below 100 nM (7, 15, 28). These are found in the range of the new proteasomal inhibitors that are currently in clinical phases (33).

Notably, the tetrapeptide-inhibitor PSI (Z-Ile-Glu(O$^t$Bu) Ala-Leu-CHO) (36) is structurally related with the compound according to the invention 15 (Z-Leu-Asp(O$^t$Bu)Leu-CHO), which belongs to the strongest inhibitors ($IC_{50}$ below 60 nM).

Furthermore, 15 exhibited a low toxicity and was able to penetrate cellular membranes.

The comparison of the inhibitors according to the invention showed that the ligand-side chains provide the main contributions to the specific and fixed interactions with the different proteolytic catalytic centres (FIG. 8 and example 10). Similar observations were made for the alcohol-derivatives, out of which compound 7 is more effective than the other six. Furthermore, very potent inhibitors were identified in the form of chloromethyl ketone (compound 22) and compounds 25-28.

Tumour cells with their accelerated neoplastic growth are often more sensitive against proteasomal inhibitors, compared with normal cells. The clinically tested proteasomal inhibitor Bortezomib® caused growth arrest and apoptosis in sensitive tumour cells, whereas "normal" cells tolerate higher inhibitor cells (37). The restriction to myeloma tumours could be overcome by more specific inhibitors, such as PSI, which blocked angiogenesis and thus modulated the growth of solid tumours (36). The differences in cellular properties and the predictable resistance-mechanisms required a continuous development of novel proteasomal inhibitors. Efficient cell-permeation, stability in aqueous systems, and the potent induction of cellular events are all obligatory for clinical uses.

Thus, the ability to permeate of the compounds according to the invention and the in vivo influence on proteasomes was tested, and an accumulation of poly-ubiquitinylated proteins in cultivated cells was observed. A more 50% reduction of the intracellular proteasomal activity was observed for 5 of the inhibitors (15, 22, 25, 26, 28) already after 20 hours of incubation. Notably, the proteasomal activity was reduced to 10% in the presence of 15, 26 and 28. Weak inhibitors have a lower influence on the cellular function. The results of the present invention show potency, membrane-permeation and sufficient stability during the incubation periods for the inhibitors 15, 22, 25, 26 and 28. The cellular proteasomal activity is unambiguously reduced and is accompanied by a strong induction of apoptosis following 20-hour treatment with 1 µM of the inhibitors (15, 26, 28). The known increased sensitivity of tumour cells against proteasomal inhibition was confirmed for inhibitor 15 and 28. Surprisingly, a strong induction of the apoptosis was observed in cells that were pre-incubated with compound 7, which inhibited the trypsin-like activity in an exclusive manner. These results indicate that the trypsin-like activity is of particular importance for anti-apoptotic processes.

According to the invention the compounds can be used for the induction of apoptosis in cells.

Furthermore, the compounds according to the invention can be used for the inhibition of the proteolytic activity of the 20S proteasome, 26S proteasome and/or immunoproteasome. Therein they are used for the in vitro, in vivo and/or intracellular inhibition.

Preferably, thereby specifically the trypsin-like activity of the 20S proteasome and 26S proteasome and/or immunoproteasome is inhibited.

Further preferred specifically the chymotrypsin-like activity of the 20S proteasome and 26S proteasome and/or immunoproteasome is inhibited.

Nevertheless, preferably also the chymotrypsin-like, trypsin-like and caspase-like activities of the 20S proteasome and 26S proteasome and/or immunoproteasome can be simultaneously inhibited.

It is furthermore preferred according to the present invention to use the compounds for the treatment of diseases, such as for the treatment of the following therapeutic fields:

Neurology

Inhibitions or malfunctions of proteasomes are associated with the development of Alzheimer's disease, Parkinson's disease, and the Pick-disease. Proteasomes are involved in amyotrophic lateral sclerosis (ALS), in diseases of motor neurons, the polyglutamine-disease and muscular dystrophies.

Tumour Diseases

Proteasomes play a role in the malign transformation, regulation of the cell cycle, inhibition or execution of apoptosis, respectively, degradation of several tumour suppressor-products (APC, p53, Rb), degradation of proto-oncogenes (Raf, Myc, Myb, Rel, Src etc.), malfunctions in the cell cycle regulation. Proteasomes are responsible for the degradation of cyclines, CDK's and inhibitors thereof; an inhibition of proteasomes in most cases leads to an arrest of the cycle.

Viral Diseases

The presentation of viral antigens requires their generation through proteasomes: e.g. HCMV, hepatitis (HCV and HBV), herpes (HVP) and others. In addition, for coxsackie (CVB) and HCMV a role of proteasomes in the viral replication is likely (39, 40)

Endocrinology

Glucocorticoids upregulate, for example, a proteasomal alpha-subunit. The degradation of proteins during the thyroxin-formation takes place through proteasomes.

Immunology

There is an involvement of proteasomes in inflammatory reactions (MHC class I ligands, induction of immunoproteasomes through cytokines). Furthermore, a possible role in the generation and the progression of autoimmune diseases exists. A determination of proteasome-antibodies is possible in the serum of SLE-, Sjögren syndrome- and polymyositis-patients, partially a detection of circulating, released proteasome in the serum of these patients is possible (41).

The present invention furthermore provides pharmaceutical compositions, comprising one or more of the compounds according to the invention or a pharmaceutically acceptable salt thereof together with pharmaceutically acceptable carriers and/or excipients. Such pharmaceutically acceptable carriers and excipients are known to the person of skill.

The pharmaceutical compositions according to the invention are characterized in that the compound(s) are present in an amount that a concentration range of preferably 0.001 to 100 µM, further preferred of 0.01 to 10 µM at the treatment in vivo.

They are furthermore characterized in that the compound(s) are present in an amount which effectively inhibits the proteasome-function in a cell or a mammal.

The present invention furthermore provides a method for the inhibition of the growth of a cancer cell, comprising contacting of a cell with a compound according to the invention or with a pharmaceutical composition according to the invention.

The present invention shall now be illustrated by the following examples with reference to the accompanying Figures, nevertheless, without being limited to the examples.

FIGURES

In the Figures

The compounds 7-28 represent the peptide-mimetics of the present invention which can be used as inhibitors of the 20S-proteasome.

Figure 1:
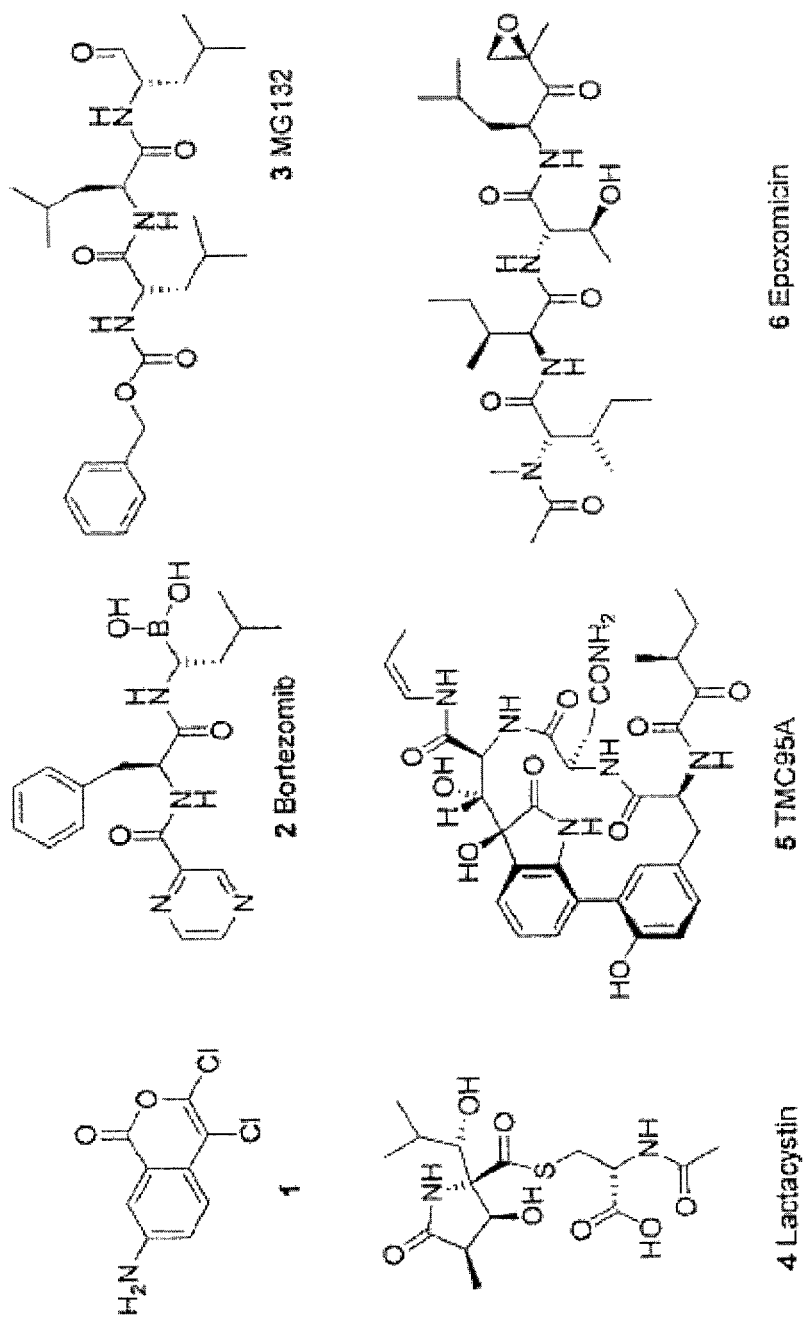
FIG. 1 shows known inhibitors of serine- and threonine-proteases.
Figure 2:
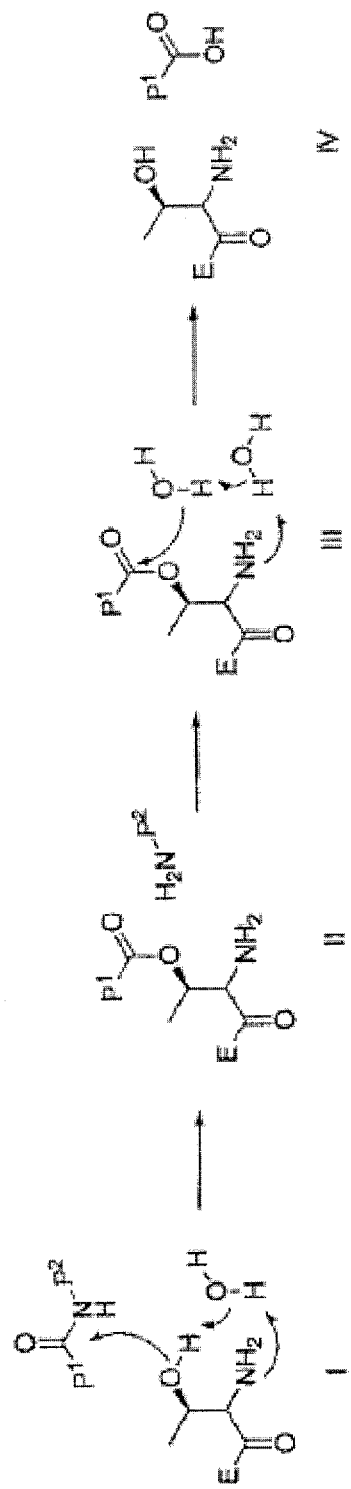
FIG. 2 shows mechanisms of the hydrolysis by threonine-proteases.
Figure 3:
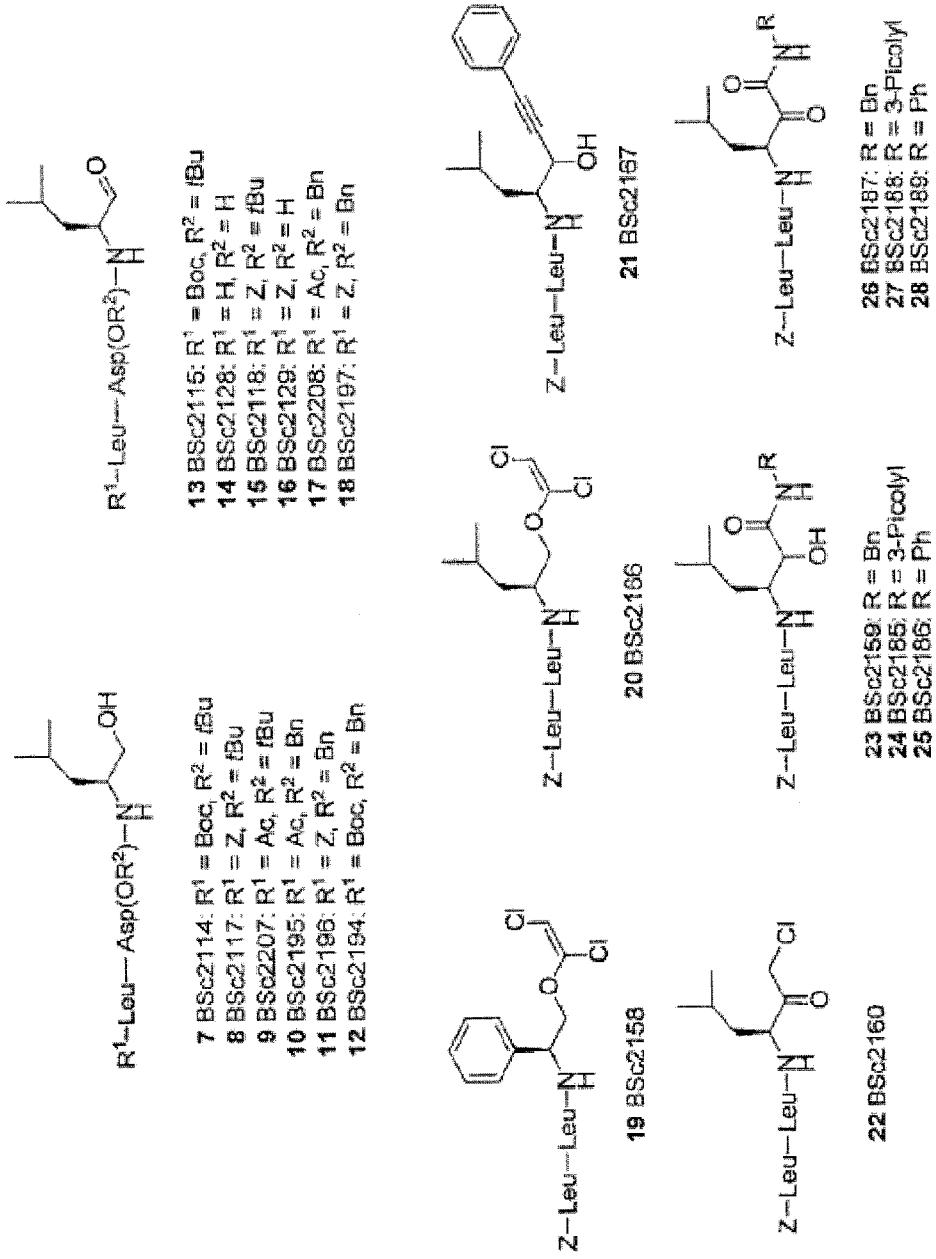
FIG. 3 shows formulae of the compounds 7-28.
Figure 4:
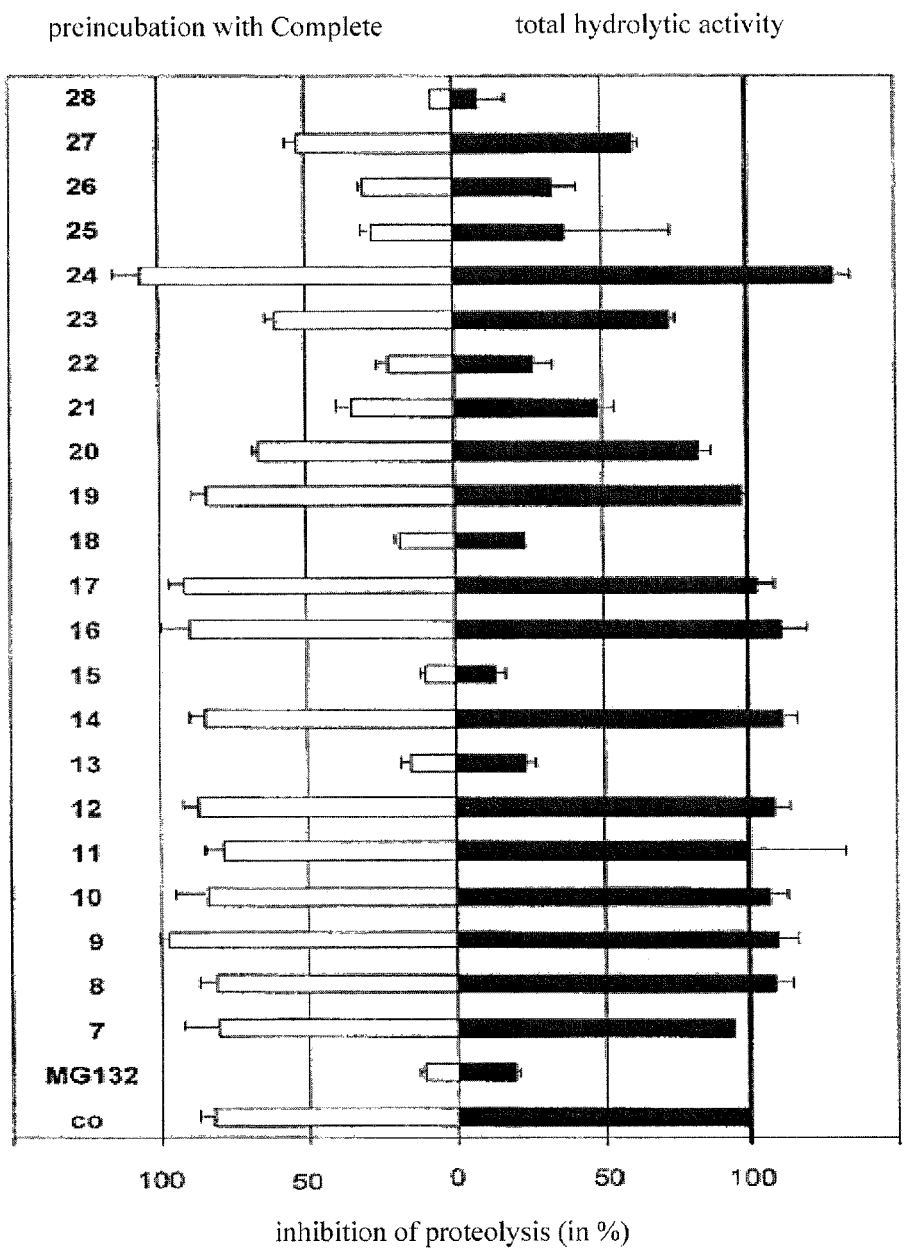

FIG. 4 shows the inhibition of the proteolysis in cellular lysates through the addition of compounds 7-28 and MG132. 10 µM of the compounds 7-28 or MG132 were added to clarified lysates, and pre-incubated for 30 min, before the proteolysis assay was performed. In parallel to this, lysate was pre-incubated for 30 min with the commercial inhibitor-mixture Complete (Roche) that inhibited most of the cytosolic serine- and aspartate-proteases, but not proteasomes. This partial inactivation was then followed by the incubation with the compounds 7-28 and MG132. The proteolytic activity was determined in 10 µl of the lysates by the addition of LLVY-AMC (100 µl, 50 µM in 20 mM Tris, pH 7.2, 1 mM EDTA, 1 mM DTT). The AMC that was released in non-inhibited lysate was set at 100%. MG132 served as inhibition control.

Figure 5:
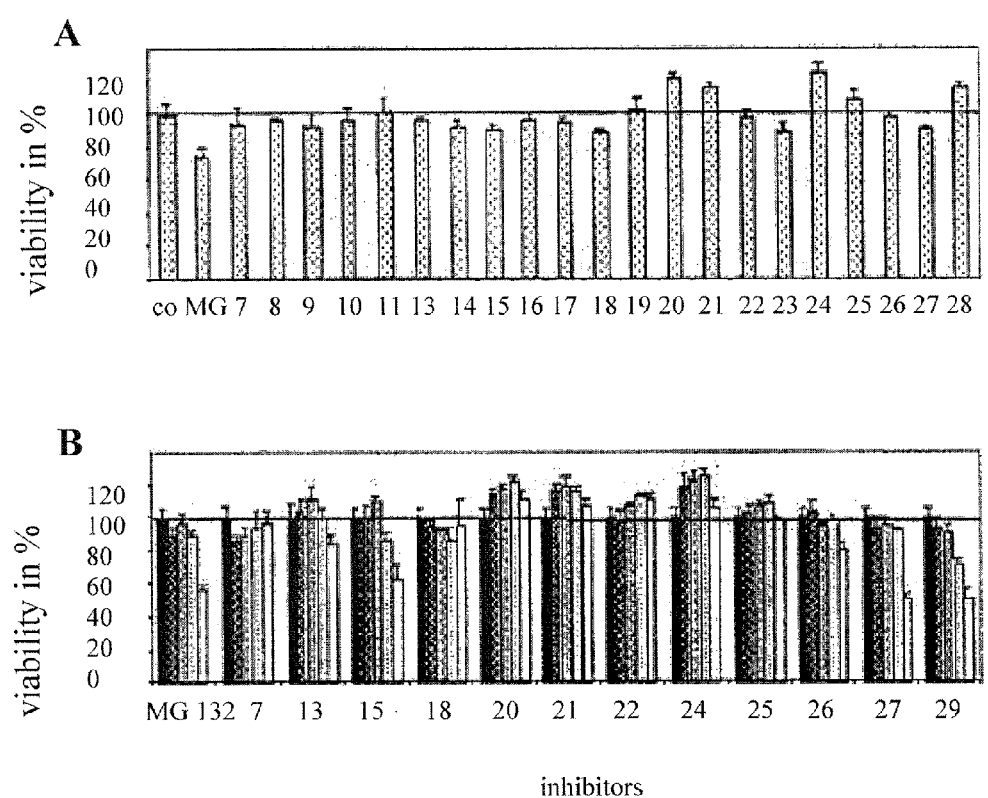

FIG. 5 Viability of HeLa-Cells following incubation with the compounds 7-28.

A, The viability of HeLa-Cells that were incubated with the compounds 7-28 and MG132 (1 µM), was determined using crystal-violet-staining after 20 h.

B, The viability of HeLa-Cells is dependent from the concentration of the inhibitor. HeLa-cells were cultivated for 20 hours in the presence of increasing concentrations (10 to 10000 nM) of the compounds (7, 13, 15, 18, 20-22, 24-28) and MG 132. The survival of the cells was determined using crystal-violet-staining.

Figure 6:
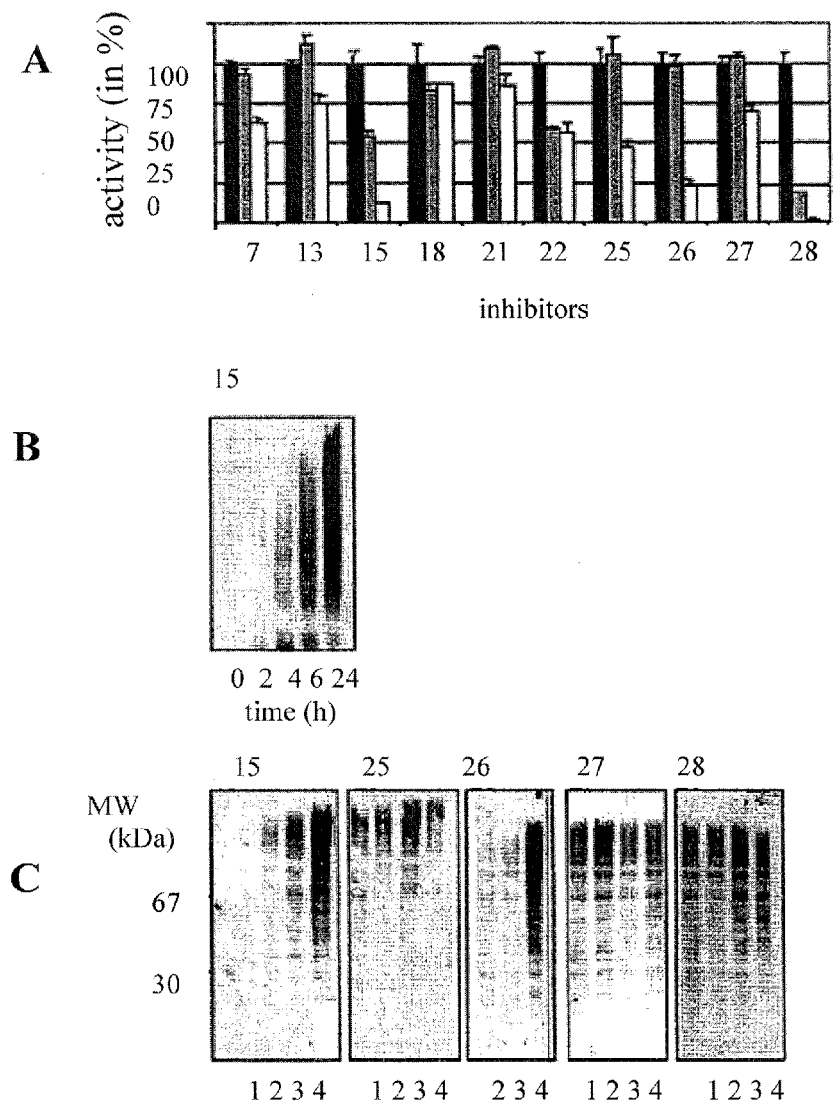

FIG. 6 Inhibition of the proteasomes in cells.

A, HeLa-cells were cultivated were 24 hours in the presence of the inhibitor. The protein concentration was determined in accordance with the cellular lysis according to Bradford in order to normalise the proteasomal activities to the different amounts of cells. Subsequently Complete (Roche) was added to all lysates, and the proteasomal activity was determined through the hydrolysis of Suc-LLVY-AMC.

B, HeLa-cells was incubated with 1 µM of compound 15 for 2, 4, 6 and 24 hours. Cells were lysed, and proteins were separated through SDS-PAGE on a 10% gel, blotted to a PVDF-membrane. The accumulation of the poly-ubiquitinylated proteins was detected in a Western blot by an anti-ubiquitine-antibody (DAKO).

C, HeLa-Cells were treated with increasing concentrations of the inhibitor 15, 25, 26, 27, and 28 for 24 hours (lane 1: without inhibitor; lane 2: 10 nM; lane 3: 100 nM and lane 4: 1 µM of the given inhibitor). Cells were lysed, proteins were separated on 15% gels, and the accumulation of the poly-ubiquitinylated proteins was controlled through Western blot.

Figure 7:
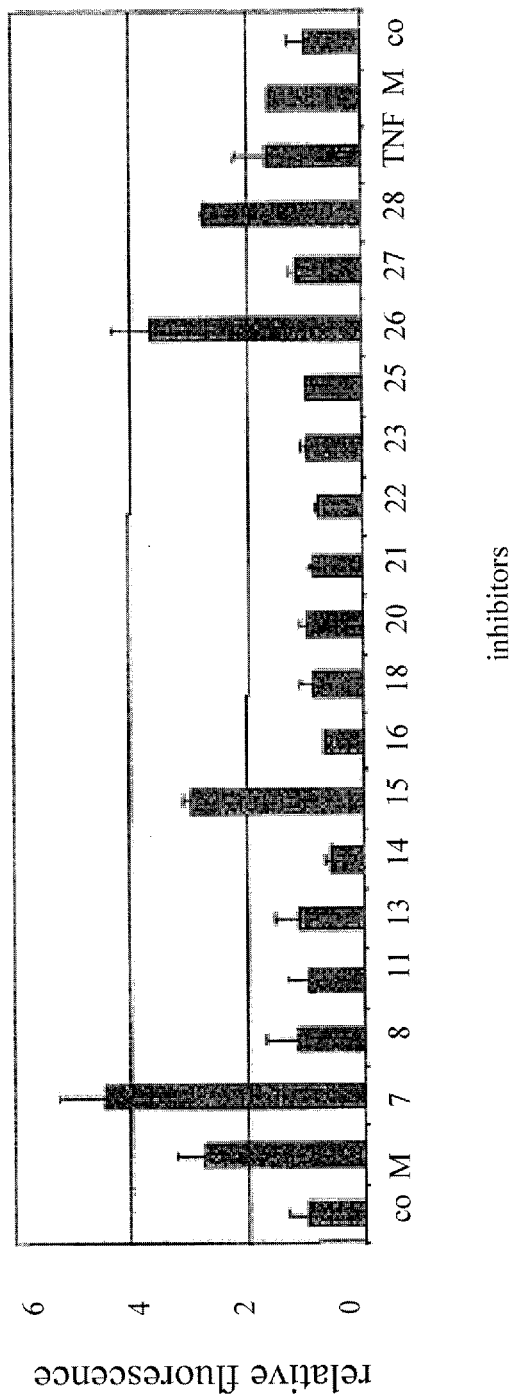

FIG. 7 The proteasome-inhibition by the compounds 7, 15, 26 and 28 leads to the induction of apoptosis.

HeLa-cells that were cultivated for 20 hours in the presence of the given inhibitor, were subsequently incubated for 2 hours with caspase-substrate (Apo-One; Promega). The activation of caspases 3/7 was measured at 538 nm (excitation at 485 nm). Treatment of the cells with TNFα or with MG132 served as control.

Figure 8:
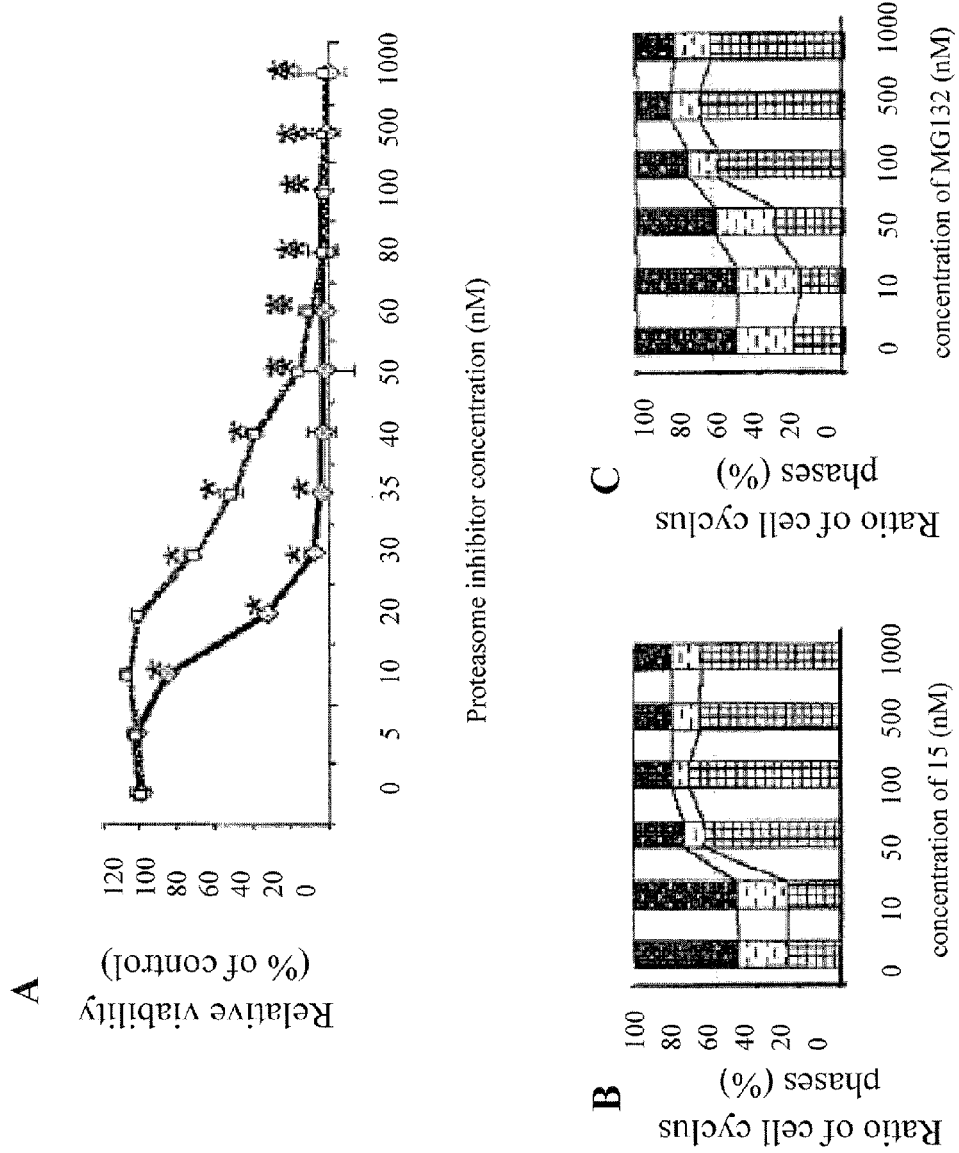

FIG. 8 Human melanoma cells showed a high sensitivity against compound 15 and examinations with respect to triggering a cell cycle arrest by compound 15.

A, Human melanoma cells (MeWo) were treated with increasing concentrations of the compounds 15 or 3 (MG132) for 72 hours. The viability of the cells after the treatment with compound 15 (-♦-) and with MG132 (-□-) was detected by a crystal-violet-staining. B and C, MeWo cells were co-cultivated with the compounds 15 and 3 (MG132) for 24 hours. The cells were subsequently fixed in 70% ethanol, and treated with RNAse A. The DNA was stained with propidium iodide (5 µg/ml), and analysed by means of FACS (FACS Calibur flow cytometer; Beckton Dickinson). The statistical significance was detected by the chi-square-test. The relative distribution of the cells that were present in the G1-(black), in the S-(white) or in the G2 phase (hatched) of the cellular cycle is shown for both compounds as examined (15 in B and MG132 in C).

Figure 9:
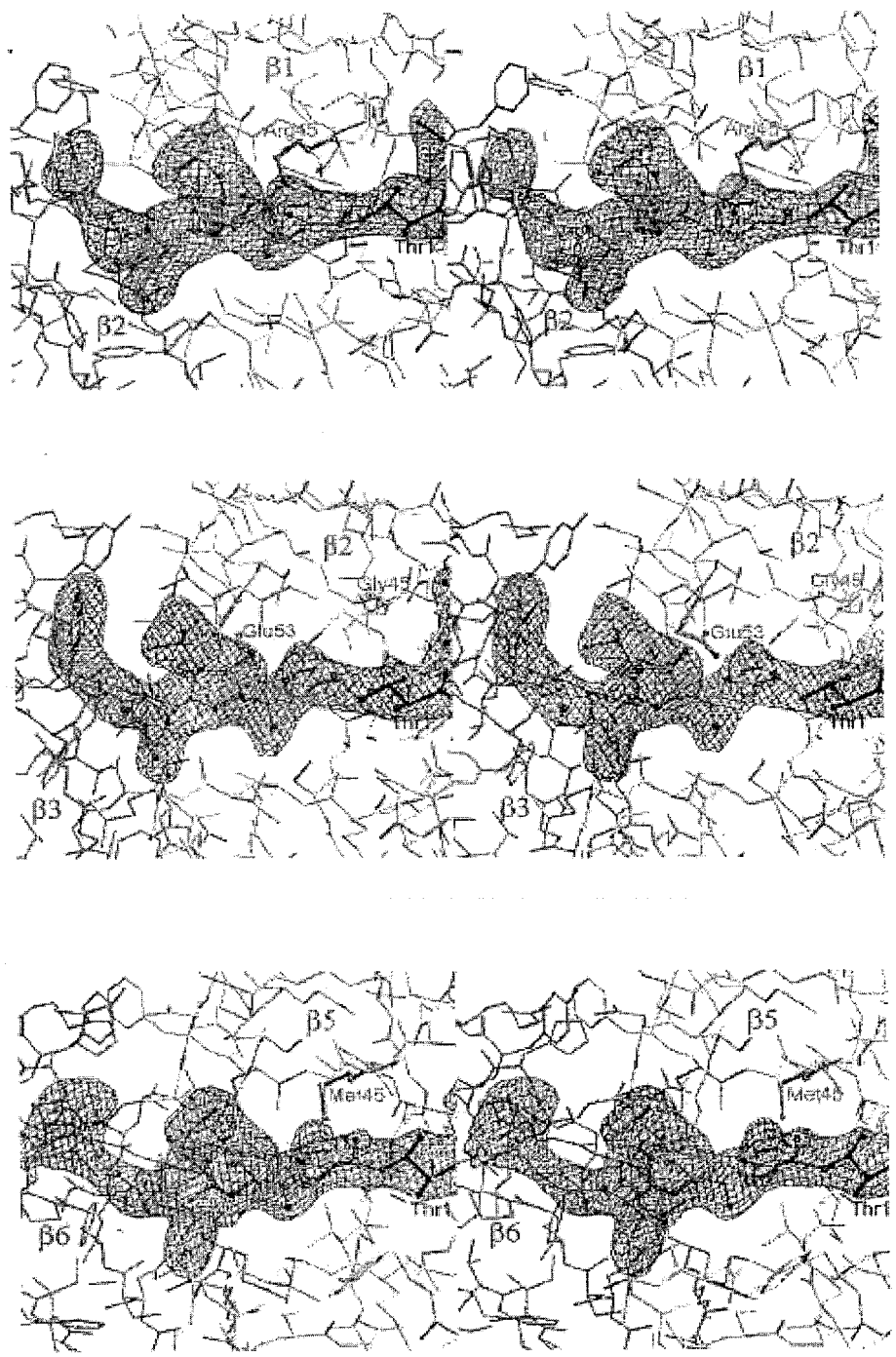

FIG. 9 Crystal structure of compound 15 with a 20S-proteasome.

Stereo view of a 30 Å-sectors of the crystal structure of the active centres of the β1 (a), β2 (b) and β5 (c)-subunits of the 20S proteasome from yeast in complex with compound 15. The aldehyde 15 is depicted for each subunit in its non-edited electron density. The Thr1 in the active centre is highlighted in black. The covalent binding between 15 and Thr1Oγ is depicted. The residues that are particularly responsible for the character of the S1-site are depicted in grey.

EXAMPLES

Example 1

Synthesis of the Compounds

A) General Matter

The $^1$H- and $^{13}$C-NMR-spectra were recorded on a Bruker AC 300 spectrometer at 300 MHz (75 MHz). The chemical shifts were given as ppm-value downstream of the field of Me$_4$Si (TMS). Mass spectrometry was performed on a Bruker-Franzen Esquire LC mass spectrometer. Flash-column chromatography was performed using Merck silicagel 60 (40-63 and 15-40 µm) and 60G (5-40 µm). Thin-layer-chromatography (TLC) was performed using aluminium plates that are coated with silicagel 60 F254 (0.2 mm; E. Merck). The chromatographic spots were visualized through UV and/or spraying with an acidic ethanolic solution of p-anisaldehyde or an ethanolic solution of ninhydrin with subsequent heating. For preparative thin-layer-chromatography, plates coated with silicagel 60 F254 (2.0 mm; E. Merck) were used. Amino acid-derivatives were obtained from Fluka Chemie (Switzerland), NovaBiochem (Switzerland) or Bachem (Switzerland). THF was dried and distilled with sodium and benzophenone. DMF was stored over 3 Å-molecular sieve. All other commercial chemicals were used without further purification.

B) Compound 7 (BSc 2114).

Ethyl-3-(3'-dimethylaminopropyl)carbodiimide hydrochloride (EDAC, 191 mg, 1.0 mmol) and N-hydroxybenzotriazole hydrate (HOBt, 183 mg, 1.2 mmol) were added to a solution of Z-Asp(OtBu)-OH (29, 323 mg, 1.0 mmol) which was dissolved in CH$_2$Cl$_2$ (10 ml). The resulting mixture was stirred at ambient temperature for 5 min, and then treated for 24 h with Z-leucinol (117 mg, 1.0 mmol) and triethylamine (151 mg, 1.5 mmol). CH$_2$Cl$_2$ (20 ml) was added, and the solution was washed with HCl (0.1 N, 5×30 ml), NaOH (0.1 N, 3×30 ml), saturated NaCl-solution (1×30 ml), dried over Na$_2$SO$_4$, and concentrated in order to obtain product 31 (350 mg, 83%). A solution of 31 (422 mg, 0.8 mmol) in ethanol (10 ml, abs.) was treated with Pd/C-catalyst (10% carbon, 100 mg) under hydrogen atmosphere at room temperature. The suspension was filtered after 3 h, and the solvent was removed under vacuum, in order to obtain compound 33 (228 mg, 100%). EDAC (157 mg, 0.82 mmol) and HOBt (132 mg, 0.98 mmol) were added to the solution of Boc-Leu-OH (189 mg, 0.82 mmol) in CH$_2$Cl$_2$ (10 ml). The resulting mixture was stirred at ambient temperature for 5 min, and then treated for 24 h with compound 33 (228 mg, 0.82 mmol) and triethylamine (124 mg, 1.23 mmol). DCM (20 ml) was added, and the solution was washed with HCl (0.1 N, 5×30 ml), NaOH (0.1 N, 3×30 ml) and saturated NaCl-solution (1×30 ml). After drying (Na$_2$SO$_4$), the solvent was removed under vacuum, in order to obtain compound 7 (BSc2114) (400 mg, 97%).

$^1$H-NMR (CDCl$_3$, 300 MHz): δ=7.65 (d, 1H, $^3$J=8.3 Hz), 6.8 (d, 1H, $^3$J=8.3 Hz), 5.03 (d, 1H, $^3$J=8.3 Hz), 4.55-4.45 (m, 1H), 3.99-3.89 (m, 2H), 3.57 (dd, 1H, $^3$J=3.3 Hz, $^2$J=11.0 Hz), 3.47 (dd, 1H, $^3$J=3.3 Hz, 2J=11.0 Hz), 2.99 (d, 1H, $^3$J=4.3 Hz), 2.58 (d, 1H, $^3$J=4.3 Hz), 2.48 (d, 1H, $^3$J=4.3 Hz), 2.15-2.14 (m, 2H), 1.44 (s, 9H), 1.34 (s, 9H), 0.90-0.87 (m, 6H), 0.80-0.75 (m, 6H) ppm.

$^{13}$C-NMR (CDCl$_3$, 75 MHz): δ=173.0, 171.5, 170.5, 156.3, 81.9, 81.0, 65.6, 54.3, 50.6, 50.5, 40.8, 39.7, 35.9, 28.4, 28.0, 24.9, 23.2, 22.2, 21.6, 21.1 ppm.

MS (EI): m/z=501 (M$^+$).

C) Compound 13 (BSc2115).

Compound 7 (BSc2114) (400 mg, 0.8 mmol) was oxidised with IBX (2-iodoxybenzoic acid, 268 mg, 0.95 mmol) in DMSO (5 ml) for 6 h at room temperature. CH$_2$Cl$_2$ (30 ml) was added, and the solution was washed with water (3×30 mL), NaHCO$_3$-solution (3×30 ml, saturated), saturated NaCl-solution (1×30 ml). After drying (Na$_2$SO$_4$), the solvent was removed under vacuum in order to obtain compound 13 (BSc2115) (390 mg, 98%).

¹H-NMR (CDCl₃, 300 MHz): δ=9.4 (s, 1H), 7.54 (d, 1H, ³J=8.3 Hz), 7.27 (d, 1H, ³J=8.3 Hz), 4.89 (d, 1H, ³J=8.3 Hz), 4.66-4.56 (m, 2H), 4.22-4.15 (m, 2H), 3.99 (dd, 1H, ³J=3.3 Hz, ²J=11.0 Hz), 2.99 (dd, 1H, ³J=3.3 Hz, ²J=11.0 Hz), 2.90 (d, 1H, ³J=4.3 Hz), 2.58 (d, 1H, ³J=4.3 Hz), 2.48 (d, 1H, ³J=4.3 Hz), 1.66-1.55 (m, 1H), 1.47-1.45 (m, 1H), 1.44 (s, 9H), 1.34 (s, 9H), 0.9-0.86 (m, 6H,), 0.80-0.76 (m, 6H) ppm.

¹³C-NMR (CDCl₃, 75 MHz): δ=200.1, 172.6, 171.6, 170.9, 156.2, 82.0, 80.8, 54.3, 50.6, 50.5, 40.8, 39.7, 35.9, 28.4, 28.0, 24.9, 23.2, 22.2, 21.6, 21.1 ppm.

MS (EI): m/z=499 (M⁺).

D) Compound 14 (BSc2128).

TFA (1 ml) was added to a stirred solution of compound 7 (BSc2114. 390 mg, 0.78 mmol) in CH₂Cl₂ (4 ml). The solvent was evaporated after 3 h, in order to obtain compound 14 (BSc2128) (260 mg, 97%).

¹H-NMR (DMSO-d₆, 300 MHz): δ=9.37 (s, 1H), 8.85 (d, 1H, ³J=8.3 Hz), 8.19 (d, 1H, ³J=8.3 Hz), 4.67-4.56 (m, 1H), 4.05-3.89 (m, 2H), 3.77-3.65 (m, 2H), 3.70-3.67 (m, 1H), 2.89 (dd, 1H, ³J=4.1 Hz, ²J=16.0 Hz), 2.78 (d, 1H, ²J=4.1 Hz, ²J=16.0 Hz), 2.58 (d, 1H, ³J=4.1 Hz), 2.48 (d, 1H, ³J=4.1 Hz), 1.60-1.58 (m, 1H), 1.46-1.44 (m, 1H), 0.80-0.76 (m, 6H), 0.70-0.66 (m, 6H) ppm.

¹³C-NMR (DMSO-d₆, 75 MHz): δ=200.1, 171.1, 171.0, 169.9, 55.2, 53.8, 50.4, 40.8, 39.7, 35.9, 23.2, 22.2, 21.6, 21.1 ppm.

MS (ESI): m/z=343.4 (M⁺).

E) The compounds 16 (BSc2129), 9 (BSc2207), 17 (BSc2208), 18 (BSc2197), and 12 (BSc2194) were produced through analogous methods.

F) Compound 8 (BSc2117).

Compound 8 was produced from compound 33 in accordance with the same procedure, and obtained with a yield of 80%.

¹H-NMR (CDCl₃, 300 MHz): δ=7.51 (d, 1H, ³J=8.3 Hz), 7.29-7.19 (m, 5H), 6.70 (d, 1H, ³J=8.3 Hz), 5.35 (d, 1H, ³J=8.3 Hz), 5.50 (s, 2H), 4.60-4.58 (m, 1H), 4.10-4.75 (m, 1H), 3.95-3.87 (m, 1H), 3.58 (dd, 1H, ³J=3.3 Hz, ²J=11.0 Hz), 3.45 (dd, 1H, ³J=3.3 Hz, ²J=11.0 Hz), 2.89 (dd, 1H, ³J=4.1 Hz, ²J=16.0 Hz), 2.80 (d, 1H, ³J=4.1 Hz, ²J=16.0 Hz), 2.59 (d, 1H, ³J=4.3 Hz,), 2.50 (d, 1H, ³J=4.3 Hz), 2.0-1.96 (m, 2H), 1.55-1.53 (m, 1H), 1.34 (s, 9H), 1.25-1.23 (m, 1H), 0.89 (dd, 6H, ³J=4.3 Hz, ³J=7.0 Hz), 0.80 (dd, 6H, ³J=4.3 Hz, ³J=7.0 Hz) ppm.

¹³C-NMR (CDCl₃, 75 MHz): δ=167.0, 166.2, 165.1, 151.4, 130.4, 123.3, 123.1, 123.1, 122.8, 77.1, 62.2, 60.2, 49.0, 45.8, 45.2, 35.6, 34.4, 31.1, 22.7, 22.7, 22.7, 21.6, 21.1, 19.5, 17.8 ppm.

MS (EI): m/z=535 (M⁺).

G) Compound 15 (BSc2118).

Compound 15 was produced from compound 8 (BSc2117) in accordance with the same procedure, and obtained with a yield of 94%.

¹H-NMR (CDCl₃, 300 MHz): δ=9.49 (s, 1H), 7.48 (d, 1H, ³J=8.3 Hz), 7.35-7.33 (m, 5H), 7.25 (d, 1H, ³J=7.3 Hz), 5.23-5.22 (m, 1H), 5.12 (s, 2H), 4.80-4.79 (m, 1H), 4.38-4.37 (m, 1H), 4.15-4.14 (m, 1H), 3.00 (d, 1H, ³J=3.3 Hz), 2.98 (d, 1H, ³J=3.3 Hz), 2.60 (d, 1H, ³J=6.3 Hz), 2.55 (d, 1H, ³J=6.3 Hz), 2.30-2.28 (m, 1H), 2.23-2.22 (m, 1H), 2.05-1.99 (m, 2H), 1.77-1.76 (m, 1H), 1.44 (s, 9H), 1.35-1.34 (m, 1H), 0.89-0.86 (m, 6H), 0.80-0.78 (m, 6H) ppm.

¹³C-NMR (CDCl₃, 75 MHz): δ=200, 172.1, 171.6, 170.8, 67.4, 156.6, 135.9, 128.7, 128.4, 128.1, 122.8, 82.1, 57.5, 54.5, 49.8, 45.8, 45.2, 41.1, 37.4, 36.5, 28.0, 28.0, 28.0, 24.5, 23.3, 23.0, 21.7 ppm.

MS (ESI): m/z=533 (M⁺).

H) Compound 16 (BSc2129).

Compound 16 was produced from compound 15 (BSc2118) in accordance with the same procedure, and obtained with a yield of 84%.

¹H-NMR (DMSO-d₆, 300 MHz): δ=9.8 (s, 1H), 9.37 (s, 1H), 8.30 (d, 1H, ³J=8.3 Hz), 8.24 (d, 1H, ³J=7.3 Hz), 7.36-7.34 (m, 5H), 5.22-5.21 (m, 1H), 5.12 (s, 2H), 4.80-4.79 (m, 1H), 4.5-4.45 (m, 1H), 4.15-4.10 (m, 1H), 3.30-3.29 (m, 1H), 2.98-2.97 (m, 1H), 2.60-2.59 (m, 1H), 2.55-2.54 (m, 1H), 2.30-2.29 (m, 1H), 2.23-2.22 (m, 1H), 2.05-1.99 (m, 2H), 1.77-1.76 (m, 1H), 1.35-1.34 (m, 1H), 0.89-0.88 (m, 6H), 0.80-0.79 (m, 6H) ppm.

¹³C-NMR (DMSO-d₆, 75 MHz): δ=200, 172.1, 171.6, 170.8, 67.4, 156.6, 135.9, 128.7, 128.4, 128.1, 122.8, 82.1, 57.5, 54.5, 49.8, 45.8, 45.2, 41.1, 37.4, 36.5, 24.5, 23.3, 23.0, 21.7 ppm.

MS (ESI): m/z=476 (M⁺).

I) Compound 9 (BSc2207).

Compound 9 was produced from compound 33 in accordance with the same procedure, and obtained with a yield of 93%.

¹H-NMR (CDCl₃, 300 MHz): δ=7.67 (d, 1H, ³J=8.3 Hz), 7.4 (d, 1H, ³J=9.2 Hz), 7.26 (d, 1H, ³J=8.4 Hz), 4.7-4.63 (m, 2H), 4.43-4.33 (m, 2H), 4.04-3.94 (m, 2H), 3.59-3.54 (m, 1H), 3.53-3.43 (m, 1H), 3.30 (dd, 1H, ³J=4.5 Hz, ²J=17.0 Hz), 2.8 (dd, 1H, ³J=4.8 Hz, ²J=17.0 Hz), 2.65-2.55 (m, 1H), 2.54-2.45 (m, 1H), 2.15-2.05 (m, 2H), 2.0 (d, 3H, ³J=15.0 Hz), 1.44 (s, 9H), 0.9-0.87 (m, 6H), 0.80-0.78 (m, 6H) ppm.

¹³C-NMR (CDCl₃, 75 MHz): δ=172.5, 172.3, 171.6, 169.9, 82.0, 66.6, 53.4, 50.4, 49.5, 40.8, 39.7, 35.9, 28.4, 25.0, 24.7, 22.9, 23.2, 22.1 ppm.

MS (EI): m/z=443 (M⁺).

J) Compound 10 (BSc2195).

Compound 10 was produced from compound 34 in accordance with the same procedure, and obtained with a yield of 88%.

¹H-NMR (CDCl₃, 300 MHz): δ=8.26 (d, 1H, ³J=7.2 Hz), 7.59 (m, 5H, ArH), 6.70 (d, 1H, ³J=7.3 Hz), 6.35 (d, 1H, ³J=7.0 Hz), 5.20 (s, 2H), 4.62-4.48 (m, 1H), 4.44-4.42 (m, 1H), 4.01-4.00 (m, 1H), 3.98-3.97 (m, 1H), 3.91-3.90 (m, 1H), 2.89-2.88 (dm, 1H), 2.80-2.78 (m, 1H), 2.59-2.58 (m, 1H), 2.50-2.49 (m, 1H), 2.0-1.99 (m, 2H), 1.55-1.54 (m, 1H), 1.34 (s, 3H), 1.25-1.24 (m, 1H), 0.89 (dd, 6H, ³J=3.8 Hz, 6.7 Hz), 0.80 (dd, 6H, ³J=3.8 Hz, 6.7 Hz) ppm.

¹³C-NMR (CDCl₃, 75 MHz): δ=175.5, 173.7, 173.0, 169.7, 128.8, 128.3, 68.5, 66.5, 41.4, 40.8, 40.2, 35.6, 34.4, 31.1, 23.5, 22.1, 23.9, 23.6, 22.9 ppm.

MS (EI): m/z=477 (M⁺).

K) Compound 17 (BSc2208).

Compound 17 was produced from compound 10 (BSc2195) in accordance with the same procedure, and obtained with a yield of 74%.

¹H-NMR (CDCl₃, 300 MHz): δ=9.40 (s, 1H), 8.26 (d, 1H, ³J=7.0 Hz), 7.28-7.19 (m, 5H), 6.70 (d, 1H, ³J=7.0 Hz), 5.65 (d, 1H, ³J=7.0 Hz), 5.30 (s, 2H), 4.82-4.81 (m, 1H), 4.35-4.33 (m, 1H), 3.96-3.95 (m, 1H), 2.80-2.79 (m, 1H), 2.75-2.74 (m, 1H), 2.49-2.48 (m, 1H), 2.45-2.44 (m, 1H), 2.0-1.98 (m, 2H), 1.51-1.50 (m, 1H), 1.30 (s, 3H), 1.25-1.24 (m, 1H), 0.89 (dd, 6H, ³J=3.8 Hz, 6.4 Hz), 0.80 (dd, 6H, ³J=3.8 Hz, 6.4 Hz) ppm.

¹³C-NMR (CDCl₃, 75 MHz): δ=200, 174.5, 173.5, 173.0, 166.7, 128.6, 128.3, 68.5, 41.4, 40.8, 40.2, 35.6, 34.4, 31.1, 23.5, 22.1, 23.9, 23.6, 22.9.

MS (EI): m/z=475 (M⁺).

L) Compound 11 (BSc2196).

Compound 11 was produced from compound 34 in accordance with the same procedure, and obtained with a yield of 77%.

¹H-NMR (CDCl₃, 300 MHz): δ=7.29-7.19 (m, 10H), 6.65 (d, 1H, ³J=7.0 Hz), 6.33 (d, 1H, ³J=7.0 Hz), 5.35 (d, 1H, ³J=7.0 Hz), 5.28-5.17 (m, 4H), 4.22-4.21 (m, 1H), 4.0-3.99 (m, 1H), 3.74-3.73 (m, 1H), 3.66-3.65 (m, 1H), 3.22-3.21 (m, 1H), 2.99-2.98 (m, 1H), 2.92-2.91 (m, 1H), 2.62-2.60 (d, 1H), 2.50-2.51 (d, 1H,), 2.4-2.3 (m, 2H), 1.57-1.56 (m, 1H), 1.24-1.23 (m, 1H), 0.87 (dd, 6H, ³J=3.8 Hz, 6.4 Hz), 0.80 (dd, 6H, ³J=3.8 Hz, 6.4 Hz) ppm.

¹³C-NMR (CDCl₃, 75 MHz): δ=172.4, 172.0, 170.2, 156.8, 142.8, 135.8, 128.7, 68.5, 67.2, 62.2, 52.0, 49.8, 49.2, 41.6, 40.4, 33.1, 22.4, 22.1, 21.6, 21.1, 19.5, 18.3 ppm.

MS (EI): m/z=569 (M⁺).

M) Compound 18 (BSc2197).

Compound 18 was produced from compound 11 (BSc2196) in accordance with the same procedure, and obtained with a yield of 74%.

¹H-NMR (CDCl₃, 300 MHz): δ=9.33 (s, 1H), 7.26-7.19 (m, 10H), 7.03 (d, 1H, ³J=7.0 Hz), 6.41 (d, 1H, ³J=7.0 Hz), 5.66 (d, 1H, ³J=7.0 Hz), 5.23-4.95 (m, 4H), 4.26-4.13 (m, 1H), 4.12-4.03 (m, 1H), 3.57-3.54 (m, 1H), 2.94 (d, 1H, ³J=7.3 Hz), 2.72 (d, 1H, ³J=7.3 Hz), 2.02 (d, 1H, ³J=10.0 Hz), 1.99 (d, 1H, ³J=10.0 Hz), 1.57-1.44 (m, 2H), 1.45-1.42 (m, 1H), 1.24-1.99 (m, 1H), 0.87 (dd, 6H, ³J=3.8 Hz, 6.4 Hz), 0.80 (dd, 6H, ³J=3.8 Hz, 6.4 Hz) ppm.

¹³C-NMR (CDCl₃, 75 MHz): δ=200, 173.4, 172.6, 171.2, 156.8, 142.8, 138.8, 128.7, 128.7, 66.5, 65.2, 52.0, 49.7, 48.2, 41.7, 40.6, 33.5, 22.6, 22.3, 21.9, 21.5, 19.4, 18.0 ppm.

MS (ESI): m/z=567 (M⁺).

N) Compound 12 (BSc2194).

Compound 12 was produced from compound 34 in accordance with the same procedure, and obtained with a yield of 90%.

¹H-NMR (CDCl₃, 300 MHz): δ=7.32-7.28 (m, 5H), 7.01 (d, 1H, ³J=1.0 Hz), 6.33 (d, 1H, ³J=7.0 Hz), 5.32 (s, 2H), 4.91 (d, 1H, ³J=7.0 Hz), 4.25-4.22 (m, 1H), 4.08-4.06 (m, 1H), 3.98-3.97 (m, 1H), 3.68-3.65 (dd, 2H), 2.99-2.97 (m, 1H), 2.92 (d, 1H, ³J=7.3 Hz), 2.59 (d, 1H, ³J=7.3 Hz), 2.50 (d, 1H, ³J=7.3 Hz), 1.97-1.87 (m, 2H), 1.55-1.54 (m, 1H), 1.34 (s, 9H), 1.24, 1.23 (m, 1H), 0.89 (dd, 6H, ³J=3.8 Hz, 6.4 Hz), 0.80 (dd, 6H, ³J=3.8 Hz, 6.4 Hz) ppm.

¹³C-NMR (CDCl₃, 75 MHz): δ=172.8, 172.4, 170.1, 155.8, 135.4, 128.6, 77.1, 76.6, 67.2, 62.2, 49.0, 45.8, 45.2, 35.6, 34.4, 33.1, 23.7, 22.4, 22.1, 21.6, 21.1, 19.5, 18.3 ppm.

MS (EI): m/z=535 (M⁺).

O) Compound 19 (BSc2158).

A suspension of NaH in mineral oil (60%, 291 mg, 7.3 mmol) in THF (2 ml, abs.) was treated with (S-(−)-phenylglycinol (500 mg, 3.6 mmol) at −15° C. under argon atmosphere, and stirred for 20 min. The mixture was cooled to −55° C. before trichloroethylene (400 μL, 4.5 mmol) in THF (2 ml) was added. The mixture was heated to ambient temperature within 5 h, water (40 ml) was added, and subsequently extracted with Et₂O (60 ml). The organic layer was extracted, washed with saturated NaCl-solution (40 ml), dried (Na₂SO₄), and concentrated. The product was purified through column chromatography, in order to give the dichlorovinylether 35 (347 mg, 56%).

To a mixture of Z-Leu-Leu-OH (378 mg, 1.0 mmol), EDAC (192 mg, 1.0 mmol) and HOBt (170 mg, 1.1 mmol), DMF (2 ml) was added. The resulting solution was vigorously stirred for 10 min, and then the dichlorovinylether 35 (200 mg, 1.2 mmol) and Et₃N (0.28 ml, 2.0 mmol) were added. The solution was stirred for 2 h. DCM (40 ml) was added and washing was performed with hydrochloric acid (0.1 N, 3×30 ml), aqueous NaHCO₃ (saturated, 3×30 ml) and water (3×30 ml). The organic phase was dried (Na₂SO₄), and the solvent was removed under vacuo in order to obtain compound 19 (BSc2158) (403 mg, 77%).

¹H-NMR (DMSO-d₆, 300 MHz): δ=8.52 (d, 1H, ³J=8.3 Hz), 8.33 (d, 1H, ³J=8.3 Hz), 7.44 (d, 1H, ³J=8.2 Hz, NH-Leu1), 7.40-7.28 (m, 10H), 6.07 (s, 1H), 5.19-5.12 (m, 1H), 5.00 (s, 2H), 4.45-4.40 (m, 1H), 4.22-4.11 (m, 2H), 4.08-4.01 (m, 1H), 1.65-1.35 (m, 6H), 0.90-0.78 (m, 12H) ppm.

¹³C-NMR (DMSO-d₆, 75 MHz): δ=172.0, 171.5, 155.8, 142.2, 138.4, 136.9, 128.2, 127.7, 127.6, 127.4, 127.5, 126.9, 97.7, 73.0, 65.2, 53.0, 51.4, 50.8, 40.8, 40.6, 24.1, 24.0, 22.6, 21.9, 21.6, 21.3 ppm.

MS (EI): m/z=480 (Z-Leu-Leu-C₈H₉⁺), 371 (C₁₀-Leu-C₁₀H₁₀Cl₂NO⁺).

P) Compound 20 (BSc2166).

The dichlorovinylether 36 (178 mg, 25%) was synthesized from (S)-(−)-leucinol (400 mg, 3.4 mmol) in accordance with the synthesis of the dichlorovinylether 35. The reaction was started at −70° C., heated over night to room temperature, and then stirred for another 60 h. The coupling of compound 36 (100 mg, 0.47 mmol) with Z-Leu-Leu-OH (100 mg, 0.47 mmol) gave product 20 (BSc2166) (143 mg, 63%).

¹H-NMR (DMSO-d₆, 300 MHz): δ=7.92 (d, 1H, ³J=5.1 Hz), 7.70 (d, 1H, ³J=5.1 Hz), 7.48 (d, 1H, ³J=4.2 Hz), 7.40-7.31 (m, 5H), 6.05 (s, 1H), 5.05 (s, 2H), 4.33-4.29 (m, 1H), 4.08-4.03 (m, 2H), 3.87-3.85 (m, 2H), 1.60-1.41 (m, 9H,) 0.90-0.88 (m, 18H) ppm.

¹³C-NMR (DMSO-d₆, 75 MHz): δ=171.9, 171.5, 155.8, 142.9, 137.0, 128.2, 127.7, 127.5, 97.9, 73.3, 65.3, 53.1, 50.9, 45.7, 40.9, 40.0, 39.8, 24.11, 24.08, 23.85, 23.16, 22.92, 22.87, 21.80, 21.50, 21.5 ppm.

MS (EI): m/z=460 (Z-Leu-Leu-C₆H₁₄N⁺), 295 (CO-Leu-C₄H₆Cl₂NO⁺).

Q) Compound 21 (BSc2167).

A round flask that was dried in an oven was loaded with Zn(OTf)₂ (168 mg, 0.45 mmol) and (−)-ephedrine (84 mg, 0.50 mmol) under argon atmosphere. Et₃N (51 mg, 70 μL, 0.50 mmol) in dry toluol (2 ml) was added and stirred for 2 h at room temperature. Compound 3 (MG132) (200 mg, 0.42 mmol) and phenylacetylene (52 mg, 56 μL, 0.50 mmol) were added after a further 15 min, and stirred for 20 h at 60° C. CH₂Cl₂ (40 ml) and an aqueous KH₂PO₄/Na₂HPO₄-buffer (30 ml, pH 5.5) were added, the organic layer was separated, and the aqueous phase was extracted with CH₂Cl₂ (2×30 ml). The unified organic layers were dried (Na₂SO₄), and the solvent removed under vacuum. The crude product was purified by means of column chromatography, in order to give compound 21 (BSc2167) (260 mg, 54%).

¹H-NMR (DMSO-d₆, 300 MHz): δ=8.46-8.37 (m, 1H), 7.50-7.47 (m, 1H), 7.43-7.19 (m, 10H), 5.20-5.11 (m, 1H), 5.00-4.95 (m, 2H), 4.57-4.49 (m, 2H), 4.13-4.03 (m, 2H), 1.80-1.24 (m, 9H), 0.90-0.53 (m, 18H) ppm.

¹³C-NMR (DMSO-d₆, 75 MHz): δ=174.2, 174.7, 156.9, 139.5, 131.2, 127.9, 127.8, 127.6, 127.3, 126.5, 126.3, 98.1, 80.0, 63.1, 62.8, 54.5, 52.9, 46.8, 40.9, 40.3, 36.9, 24.7, 24.2, 24.0, 23.2, 23.1, 22.9, 21.4, 21.2, 20.7 ppm.

MS (EI) m/z=446 (Z-Leu-Leu-C₅H₁₁⁺), 257 (CO-Leu-C₆H₁₃O⁺).

R) Compound 22 (BSc2160).

Z-Leu-Leu-OH (151 mg, 0.4 mmol) and (S)-3-Amino-1-chlor-5-methylhexan-2-on (80 mg, 0.4 mmol) were coupled as described for compound 19 (BSc2158). The crude product was purified by means of column chromatography, in order to give compound 22 (BSc2160) (32 mg, 16%).

¹H-NMR (CDCl₃, 300 MHz): δ=7.35-7.19 (m, 5H), 6.81-6.73 (m, 1H), 6.41-6.32 (m, 1H), 5.16 (d, 1H, ³J=5.1 Hz), 5.03

(s, 2H), 4.64-4.61 (m, 1H), 4.35-4.06 (m, 3H), 1.87-1.40 (m, 9H), 0.92-0.73 (m, 18H) ppm.

$^{13}$C-NMR (CDCl$_3$, 75 MHz): δ=201.4, 172.7, 172.3, 156.6, 136.2, 128.6, 128.3, 128.0, 67.2, 55.0, 53.8, 51.8, 47.1, 41.4, 40.6, 39.6, 24.9, 24.8, 23.3, 22.9, 22.7, 22.6, 22.3, 22.2, 21.5 ppm.

MS (EI): m/z=488 (Z-Leu-Leu-Leu-CH$_2^+$), 432 (OCO-Leu-Leu-Leu-CH$_2$Cl$^+$).

S) Compound 23 (BSc2159).

Compound 3 (MG132) (300 mg, 0.63 mmol), benzylisonitrile (116 µl, 0.95 mmol), and pyridine (204 µl, 2.53 mmol) were dissolved in CH$_2$Cl$_2$ (2.0 ml), and cooled to −10° C. Trifluoroacetic acid (97 µl, 1.26 mmol) was added dropwise under argon atmosphere for over 15 min (T<0° C.). The cooling was continued for 2 h, after which additional 72 h followed at room temperature. CH$_2$Cl$_2$ (50 ml) was added, and washing took place with hydrochloric acid (0.1 N, 3×30 ml), aqueous NaHCO$_3$ (saturated, 3×30 ml) and saturated NaCl-solution (3×40 ml). The organic phase was dried (Na$_2$SO$_4$), and the crude product was purified by means of column chromatography, in order to give compound 23 (BSc2159) (191 mg, 50%).

$^1$H-NMR (CDCl$_3$, 300 MHz): δ=7.51-7.27 (s, 1H), 7.26-7.14 (m, 10H), 6.91-6.80 (m, 1H) 5.82-5.63 (m, 2H), 5.02-4.90 (m, 2H), 4.35 (d, 1H, $^3$J=10.7 Hz), 4.30-4.01 (m, 5H), 1.55-1.31 (m, 9H), 0.81-0.73 (m, 18H) ppm.

$^{13}$C-NMR (CDCl$_3$, 75 MHz): δ=173.3, 172.7, 172.6, 157.5, 138.0, 136.2, 128.9, 128.8, 128.6, 128.1, 127.9, 127.8, 73.5, 67.3, 53.9, 52.0, 51.7, 43.2, 42.4, 41.6, 25.0, 24.8, 23.3, 23.0, 22.1, 22.0, 21.6 ppm.

MS (EI): m/z=610 (M$^+$).

T) Compound 24 (BSc2185).

Compound 3 MG132 (145 mg, 0.3 mmol) and 3-picolyl-isonitrile (52 mg, 0.45 mmol) were converted in accordance with the preparation of compound 23 (BSc2159) into the α-hydroxylamide 24 (BSc2185). The purification by means of column chromatography gave compound 24 (BSc2185) (103 mg, 56%).

$^1$HNMR (CDCl$_3$, 300 MHz): δ=8.62-8.36 (m, 2H), 7.71-7.50 (m, 2H), 7.28-7.20 (m, 6H), 7.05-6.96 (m, 1H) 5.92-5.57 (m, 2H), 5.00 (s, 2H), 4.72-4.56 (m, 1H), 4.46-4.10 (m, 5H), 1.79 (s, 1H), 1.62-1.18 (m, 9H), 0.92-0.73 (m, 18H) ppm.

$^{13}$C-NMR (DMSO-d$_6$, 75 MHz): δ=172.4, 171.9, 171.2, 155.8, 148.9, 147.9, 137.0, 135.2, 135.0, 128.2, 127.7, 127.6, 123.2, 73.8, 65.2, 53.0, 51.0, 49.2, 42.8, 40.6, 37.1, 24.1, 23.7, 22.2, 23.0, 21.8, 21.7, 21.6, 21.1 ppm.

MS (EI) m/z=611 (M$^+$).

U) Compound 25 (BSc2186).

Compound 3 MG132 (200 mg, 0.42 mmol) and phenyl-isonitrile (65 mg, 0.63 mmol) were converted in accordance with the preparation of compound 23 (BSc2159) into the α-hydroxylamide 25 (BSc2186). The crude product was purified by means of column chromatography, in order to give compound 25 (BSc2186) (70 mg, 28%).

$^1$H-NMR (DMSO-d$_6$, 300 MHz): δ=8.27 (s, 1H). 7.72-7.57 (m, 2H), 7.37-7.20 (m, 7H), 7.11-7.01 (m, 2H), 6.11-6.08 (m, 1H), 5.95-5.92 (m, 1H), 5.07 (s, 2H), 4.30-4.24 (m, 2H), 4.07-3.99 (m, 2H), 1.57-1.32 (m, 9H), 0.88-0.61 (m, 18H) ppm.

$^{13}$C-NMR (DMSO-d$_6$, 75 MHz): δ=172.0, 171.1, 171.0, 155.7, 138.3, 137.0, 128.4, 128.2, 127.6, 127.5, 123.5, 119.5, 65.2, 52.7, 52.9, 49.2, 40.5, 40.3, 40.0, 24.1, 23.9, 23.8, 23.1, 23.0, 22.6, 22.0, 21.3, 21.2 ppm.

MS (EI) m/z=596 (M$^+$).

V) Compound 26 (BSc2187).

α-Hydroxylamide 23 (BSc2159) (40 mg, 0.065 mmol) and IBX (36 mg, 0.13 mmol) were dissolved in DMSO, and stirred for 12 h at room temperature. DCM (40 ml) and water (30 ml) were added before the filtration. The organic layers were separated, washed and with water (2×40 ml), aqueous NaHCO$_3$ (1×40 ml, 0.05 N) and water (1×30 ml). The organic layer was dried (Na$_2$SO$_4$), and das solvent removed under vacuum, in order to give compound 26 (BSc 2187) (22 mg, 56%).

$^1$H-NMR (CDCl$_3$, 300 MHz): δ=7.50-7.41 (m, 1H), 7.41-7.14 (m, 10H), 6.91-6.80 (m, 1H) 5.58-5.54 (m, 1H), 5.27-5.21 (m, 1H), 5.03-4.94 (m, 2H), 4.43-4.31 (m, 3H), 4.19-4.03 (m, 2H), 1.64-1.12 (m, 9H), 0.92-0.74 (m, 18H) ppm.

$^{13}$C-NMR (CDCl$_3$, 75 MHz): δ=191.8, 172.6, 171.8, 161.4, 156.4, 136.9, 136.3, 128.9, 128.9, 128.6, 128.3, 128.1, 128.0, 67.2, 53.6, 53.3, 51.6, 43.4, 41.5, 40.86, 40.0, 25.3, 24.8, 23.8, 23.7, 23.3, 23.0, 22.8, 22.4, 22.1, 21.5 ppm.

MS (EI) m/z=474 (Z-Leu-Leu-C$_6$H$_{12}$NO$^+$).

W) Compound 27 (BSc2188).

Compound 24 (BSc2185) was oxidised in accordance with the synthesis of compound 26 (BSc2187). The purification by means of column chromatography gave compound 27 (BSc2188) (60 mg, 49%).

$^1$H-NMR (CDCl$_3$, 300 MHz): δ=8.46-8.44 (m, 2H), 7.64-7.47 (m, 2H), 7.24-7.12 (m, 6H), 6.85-6.82 (m, 1H), 5.54-5.47 (m, 1H), 5.22-5.15 (m, 1H), 5.04-4.93 (m, 2H), 4.46-3.99 (m, 4H), 1.62-1.16 (m, 9H), 0.92-0.76 (m, 18H) ppm.

$^{13}$C-NMR (CDCl$_3$, 75 MHz): δ=196.4, 172.6, 171.9, 159.8, 156.4, 149.3, 149.2, 136.2, 135.9, 133.0, 128.7, 128.3, 128.0, 123.8, 67.2, 53.7, 53.3, 51.5, 41.4, 40.8, 40.6, 39.9, 25.0, 24.8, 23.3, 23.0, 22.1, 22.0 ppm.

MS (EI): m/z=609 (M$^+$), 474 (Z-Leu-Leu-C$_6$H$_{12}$NO$^+$).

X) Compound 28 (BSc2189).

Compound 25 (BSc2185) (200 mg, 0.35 mmol) was oxidised in accordance with the synthesis of compound 26 (BSc2187). The purification by means of column chromatography gave compound 28 (BSc2189) (30 mg, 50%).

$^1$H-NMR (CDCl$_3$, 300 MHz): δ=8.58 (s, 1H), 7.56-7.54 (m, 2H), 7.29-7.19 (m, 7H), 7.11-7.00 (m, 1H), 6.75 (d, 1H, $^3$J=9.0 Hz), 6.63 (d, 1H, $^3$J=9.1 Hz), 5.36-5.28 (m, 2H), 5.07 (s, 2H), 4.51-4.41 (m, 1H), 4.19-4.11 (m, 1H), 1.97-1.41 (m, 9H), 0.93-0.77 (m, 18H) ppm.

$^{13}$C-NMR (CDCl$_3$, 75 MHz): δ=196.8, 172.5, 171.8, 157.2, 156.4, 136.3, 136.2, 129.3, 129.2, 128.7, 125.5, 120.0, 67.3, 53.7, 53.0, 51.6, 41.3, 40.6, 40.9, 25.4, 25.4, 24.8, 23.3, 23.0, 22.8, 22.2, 22.1, 21.5 ppm.

MS (EI): m/z=474 (Z-Leu-Leu-C$_6$H$_{12}$NO$^+$).

Example 2

Isolation of Proteasomes

Proteasomes were isolated from red blood cells. Cells were lysed with DTT (1 mM), and the stroma-free supernatant was loaded on DEAE-sepharose (Toyopearls). Proteasome was eluted with an NaCl-gradient in TEAD (20 mM TrisCl pH 7.4, 1 mM EDTA, 1 mM azide, 1 mM DTT) of 100 to 300 mM NaCl. Proteasome was concentrated using ammonium sulfate-precipitation (between 40 and 70% saturation) and was separated in a 10-40% sucrose-gradient through centrifugation at 40.000 rpm for 16 hours (SW40; L7, Beckman & Coulter). Finally, the proteasomes were purified on a MonoQ-column and eluted with an NaCl-gradient at about 280 mM NaCl. The fractions containing purified proteasome were dialysed against 50 mM NaCl in TEAD and stored on ice. The purity was determined using SDS-PAGE.

Example 3

Protease-Assays

Suc-LLVY-AMC, Z-VGR-AMC and LLE-AMC (BACHEM, Calbiochem) was used, in order to determine the chymotrypsin-like, trypsin-like or caspase-like (post-acidic)-activities of the proteasome. Substrate was incubated with proteasome at 37° C. in assay-buffer (20 mM Tris/Cl, pH 7.2, 1 mM EDTA, 1 mM DTT) for one hour. 100 ng proteasome was pre-incubated with 0.01-10 μM of the inhibitor for 15 mm. The reaction was started by the addition of substrate (50 μM). The AMC as released was detected using fluorescence emission at 460 nm (excitation at 390 nm) using a TECAN-fluorimeter. The activity was calculated in fluorescence-units. The inhibition is depicted by $IC_{50}$-values.

Example 4

Cell Culture

HeLa-Cells were cultivated in RPMI, supplemented with 10% FCS and penicillin/streptomycin, at 5% $CO_2$. Inhibitors were administered from 100×-stock solutions (in DMSO) at the final concentrations as indicated, and incubated with the cells for at least 20 hours.

Example 5

Intracellular Inhibition of Proteasomes

All peptide-mimetics (7-28) were tested for their ability to inhibit the 20S proteasome. For this, first the inhibition of the soluble cellular proteases was examined.

10 μM solutions of the compounds 7 to 28 were added to the cytosolic fraction of HeLa-cells and incubated for 30 min on ice. Subsequently, the proteolytic process was followed through the addition of the peptide-substrate Suc-LLVY-AMC. In parallel to this, the cytosolic fraction was treated with the protease-inhibitor-cocktail Complete (Roche), which has a broad specificity, before the addition of the substrate. This inhibitor-cocktail did not influence the proteasomal activity. 11 of the 22 compounds as examined reduced the proteolysis of the cytosolic fraction as well as in the Complete-pre-treated lysate (FIG. 4). The rates of inhibition differed drastically. Some of the compounds showed no inhibition, whereas 5 of the compounds as analysed reduced the hydrolysis of Suc-LLVY-AMC by more that 75%.

Cultivated cells (HeLa) were harvested lysed and with 0.1% NP40 in TEAD in the presence of the commercially available protease-inhibitor-mixture Complete (Roche). The proteasomal activity was measured in 10 μl of the lysate using Suc-LLVY-AMC as a substrate. The protein content was quantified by means of Bradford (Protein assay; BioRad).

Example 6

Specificity of the Compounds in the 20S Proteasome-Inhibition

In order to verify that the inhibitory effect that was observed in the cytosolic fraction was caused by the inhibition of the proteasome, the inhibitors were added in different concentrations to isolated 20S proteasomes. The effects thereof were compared with the one of the commonly used proteasomal inhibitor 3 (MG132). The chymotrypsin-like (Suc-LLVY-AMC), the trypsin-like (Bz-VGR-AMC), and the caspase-like (Z-LLE-AMC)-activities of 20S proteasomes were determined following incubation for one hour at 37° C. The results are listed in table 1.

The most potent inhibitory effects were observed for the chymotrypsin-like activity. Six of the inhibitors as tested (compounds 13, 15, 25, 26, 27, 28) showed $IC_{50}$-values of less than 1 μM. The inhibition of the trypsin-like activity was less than 1 μM for the inhibitors 7, 13 and 15. Only compounds 7 and 8 exhibited an exclusive inhibition of the trypsin-like activity. The inhibition of the caspase-activity was even weaker (see table 1).

The proteasomes that are isolated from HeLa-cells mainly include proteasomes with constitutive subunits. Thus, we repeated the inhibition-experiments with immunoproteasomes that were isolated from stably transfected T2.27 cells. Immunoproteasomes exhibited a similar sensitivity against our compounds (data not shown).

TABLE 1

Calculated $IC_{50}$-values of the compounds 7-28.

| Compound | No. of Compound | β5 Chymotrypsin-like (Y) | β5 Chym.-like (L) | β2 Trypsin-like (R) | β1 Caspase-like (E) |
|---|---|---|---|---|---|
| 7 | BSc2114 | >10 | — | 0.053 | >10 |
| 8 | BSc2117 | >10 | — | 5.481 | >10 |
| 9 | BSc2207 | >10 | | — | — |
| 10 | BSc2195 | >10 | | — | — |
| 11 | BSc2196 | >10 | | — | — |
| 12 | BSc2194 | >10 | | — | — |
| 13 | BSc2115 | 0.382 | 0.102 | 0.495 | 0.098 |
| 14 | BSc2128 | >10 | >10 | >10 | >10 |
| 15 | BSc2118 | 0.058 | 0.031 | 0.155 | 1.791 |
| 16 | BSc2129 | 7.26 | — | >10 | >10 |
| 17 | BSc2208 | — | — | — | — |
| 18 | BSc2197 | 1.731 | — | — | 3.122 |
| 19 | BSc2158 | — | — | — | — |
| 20 | BSc2166 | >10 | | >10 | >10 |
| 21 | BSc2167 | 1.303 | >10 | — | — |
| 22 | BSc2160 | 2.196 | — | — | — |
| 23 | BSc2159 | — | — | — | — |
| 24 | BSc2185 | — | — | — | — |

TABLE 1-continued

Calculated IC$_{50}$-values of the compounds 7-28.

| | | IC$_{50}$ (µM) | | | |
|---|---|---|---|---|---|
| Compound | No. of Compound | β5 Chymotrypsin-like (Y) | β5 Chym.-like (L) | β2 Trypsin-like (R) | β1 Caspase-like (E) |
| 25 | BSc2186 | 0.981 | — | | 4.04 |
| 26 | BSc2187 | 0.441 | — | | 1.72 |
| 27 | BSc2188 | 0.350 | — | | 7.966 |
| 28 | BSc2189 | 0.072 | — | | >10 |
| 3 | MG132 | 0.0242 | 2.240 | 9.215 | 2.288 |

The IC$_{50}$-values form the inhibition of the proteasome were calculated at increasing concentrations of the inhibitor. The samples were pre-incubated for 15 min in ice. The assay was started through the addition of 50 µM of one of the following fluorogenic peptide substrates:

| LLVY-MCA and GLL-MCA | for chymotrypsin-like activity, |
|---|---|
| VGR-MCA | for trypsin-like activity |
| LLE-MCA | for caspase-like activity. |

The release of MCA was determined at 460 nm emission (excitation 390 nm). The IC$_{50}$-values as calculated for MG132 served as controls.

Example 7

Sensitivity of Cells Against the Compounds as Added

Protease-inhibitors are often very toxic for organisms or individual cells (1). Thus, selected inhibitors were tested in cell cultures.

The viability of Hela-Cells in the presence of different compounds was tested in 24 hour-cultures. The viability of HeLa-cells was tested through crystal violet-staining following the incubation with the inhibitors. The cells were washed once with PBS, fixed with 1% glutardialdehyde for 30 min, and washed again. Finally, the fixed cells were stained with 0.1% crystal violet in PBS for 30 min, and subsequently carefully washed with water, in order to remove unbound dye. The residual dye was eluted with 0.1% Triton X-100 in PBS, and determined at 550 nm.

HeLa-cells tolerated 1 µM concentrations of inhibitory and inactive substances (FIG. 5A). The rate of survival was markedly reduced at 10 µM-solutions, in particular for the most potent inhibitors (compounds 15, 28, 27) (FIG. 5B).

An application on cell cultures or animals requires that the concentrations of the inhibitors are chose as low as required. The specific proteasomal activity was reduced to a value of below 50% in cells that were treated with 1 µM of the compounds 15, 22, 25, 26, or 28, respectively (FIG. 6A). A markedly reduction of the specific activity was observed for compounds 7, 13 and 27. Compounds 18 and 21 showed only a very weak inhibition of the proteasomal activity (data not shown). Notably, a reduction of the proteolytic activity was observed even at a concentration of 10 nM of the compounds 15, 22 and 28.

Example 8

Detection of Accumulated Poly-Ubiquitinylated Proteins

A specific inhibition of the proteasome lead to an accumulation of poly-ubiquitinylated proteins. Indeed, the amount of poly-ubiquitinylated proteins increased during the incubation with the inhibitors. First effects were observed after 2 hours, for compound 15 (FIG. 6B) as well as for compounds 20, 22, 25 and 28 (data not shown). The results for compounds 15, 25, 26, 27 and 28 after 24 hours of incubation are shown in FIG. 6C.

50 µg of whole-cell-lysate were separated by SDS-PAGE, and blottet onto a PVDF-membrane (Millipore). The blots were blocked by means of a 5% milk-suspension. The poly-ubiquitinylated proteins were detected by anti-ubiquitin-antibody (DAKO), and anti-rabbit, POD-labelled, as a secondary antibody (DIANOVA), and visualized through ECL.

Example 9

Apoptosis-Assay

Proteasome determine the sensitive balance between life and death of the cells by controlling the transcription factors and the proteins that are involved in apoptosis. The reduction of proteasomal activity could lead to the initiation of apoptosis, as was reported for the proteasomal inhibitor 3 (MG132) (29).

For this, 10,000 HeLa-cells pro well were seeded in a 96-well-plate, and co-cultivated for 20 hours with 1 µM of the inhibitors 7, 8, 11, 13-16, 18, 20-23 and 25-28. The induction of apoptosis was determined by measuring of the caspase 3/7-activity (Apo-One®-Assay, Promega).

The treatment of cells with den most of the inhibitor resulted in a reduction of the cellular viability. For the inhibitors 7, 15, 26 and 28 a beginning apoptosis by the activation of caspase 3 and 7 could be shown as a cause for the reduced viability (FIG. 7).

Similar results were observed through fluorescence microscopy of DAPI-stained core-fragmentation (data not shown).

Example 10

Tumour Cells Show a Higher Sensitivity Against Inhibitors

Human melanoma cells (MeWo) were incubated for 72 h with different concentrations of the inhibitor 15 and 28, and the viability of the cells was determined by means of crystal violet-staining (FIG. 8). A rate of survival of 50% of the cells was observed for the compound 15 at a concentration of 15 nM, compared to 3 (MG132) with 35 nM. Fibroblasts that were treated with both compounds as a control, showed a 50% reduction of the viability under identical conditions at about 500-1000 nM.

Similar results were obtained for compound 28 (data not shown).

Example 11

Examinations Zum Cell Cyclearrest

Human melanoma cells (MeWo) were with the compounds 15 and 3 (MG132) for 24 hours co-cultivated. The cells were washed with PBS, in 70% ethanol fixed and subsequently treated with RNAse A. The DNA was stained with propidium iodide (5 μg/ml) and analysed by means of flow-cytometry (FACS Calibur flow cytometer; Beckton Dickinson). The relative dispersion of the cells that were present in different phases of the cell cycle, could thus be detected. Under the above conditions, an arrest of the cell cycle in the G2 phase could be observed using 50 nM of the inhibitors 15. In comparison, for a G2-cycle-arrest in the same cells 100 nM 3 (MG132) were required (FIG. 8 B, C). The statistical significance was detected by the Chi-square test.

Example 12

Co-Crystallisation

Furthermore, the crystal structure of the 20S yeast-proteasome in complex with the inhibitor 15 was determined.

For this, crystals of the 20S proteasome of *S. cerevisiae* were generated in hanging drops at 24° C., as described earlier (6), and incubated for 60 min with compound 15. The protein concentration as used for the crystallization was 40 mg/ml in Tris-HCl (10 mM, pH 7.5), and EDTA (1 mM). The drops contained 3 μl protein and 2 μl reservoir-solution, containing 30 mM magnesium acetate, 100 mM morpholino ethanesulfonic acid (pH 7.2) and 10% MPD.

The space group belonged to $P2_1$ with cellular dimensions of a=135.8 Å, b=300.1 ÅA, c=144.4 Å, and ($\beta$=113.1°). Data for 2.8 Å were collected using synchrotron-radiation with $\lambda$=1.05 Å on the BW6-beamline of the DESY, Hamburg, Germany. Crystals were soaked in a cryo-protecting buffer (30% MPD, 20 mM magnesium acetate, 100 mM morpholino ethanesulfonic acid pH 6.9), and frozen and in a stream of liquid nitrogen gas at 90K (Oxford Cryo Systems). X-ray-intensities were evaluated using the MOSFILM program-package (Version 6.1), and data reduction was performed with CCP4 (24). The anisotropy of the diffraction was corrected by a general anisotropic temperature factor through comparison of the observed and calculated structure-amplitudes using the program X-PLOR (25). An overall number of 2383416 reflexions that led to 248616 unique reflexions (96.9% completeness), was collected. The corresponding $R_{merge}$ was 8.7% at 2.8 Å resolution (41.9%) for the last resolution-shell). Electron density was improved trough the generation of mean values, and retransformation of the reflexions 10 times over the twofold, non-crystallographic symmetrical axis, using the program-package MAIN (26). Conventional crystallographic solid bodies, positional and temperature factor-refinements were performed with X-PLOR using the structure of the yeast-20S-proteasome as a starting model (6). For modelling, the program MAIN was used. The structure was refined to an R-factor of 21.7% (free R-factor 24.9%) with rms-deviations from the target-values of 007 Å for bond and 1.30° for angle (27).

Modelling-experiments were performed using the coordinates des yeast-20S-proteasome with the program MAIN (26).

The data show that compound 15 binds in a similar orientation to the threonine in the active centre, as was observed for the calpain-inhibitor I (6). A defined electron-density was found in all active centres, indicating that compound 15 has no specificity for the subunits at high concentrations of the inhibitors (10 mM). The functional aldehyde of the inhibitor forms a covalent hemiacetal bond with the $Thr1O^\gamma$. The peptide-backbone of 15 takes a ($\beta$-conformation, fills the gap between the $\beta$-strands, and generates an anti-parallel $\beta$-sheet-structure (FIG. 8). The side chain of the leucine directs into the S1-pocket, whereas the P2-side chain is not in contact with the protein. The side chain of the leucine in P3 closely interacts with the amino acids of the neighbouring $\beta$-subunit. In general, S1 and S3-specificity-pockets play a dominant role in the inhibitor-binding, as also observed in the crystal structures of 20S proteasome in complex with lactacystine (6) and vinylsulfone (30). The neutral character of Met45 in the subunit $\beta$5 plays a dominant role for the specificity of this subunit. The crystallographic data (FIG. 9) indicate that the P1-Leu-side chain of compound 15 causes a structural conversion of Met45. In contrast to the crystal structure of the proteasome in complex with lactacystine, Met45 is shifted by 3 Å, avoiding a contact with the leucine-side chain in P1 of compound 15, rendering the S1-pocket more spacious. Notably, the hydrophobic interactions between the leucine-residue of the inhibitor and Met45 are only weak, whereby the average residential time of the compound in the active centre is reduced. The specificity of the $\beta$1- and $\beta$2-pockets is defined by positive or negative charges that destabilise protein-ligand-interactions. Nevertheless, the inherent reactivity of the aldehyde in compound 15 causes a binding in all proteolytic active centre. The functional group of this inhibitor takes over a dominant role at binding.

LITERATURE

1. Adams, J.; Proteasome Inhibitors in Cancer Therapy, Humana Press Inc., Totowa, N. J., (2004), p. 77-84.
2. Glickman, M. H., and Ciechanover, A. (2002) *Physiological Reviews* 82, 373-428
3. Voges, D., Zwickl, P., and Baumeister, W. (1999) *Ann. Rev. Biochemistry* 68, 1015-1068
4. Peters, J. M., Cejka, Z., Harris, J. R., Kleinschmidt, J. A., and Baumeister, W. (1993) *Journal of Molecular Biology* 234, 932-937
5. Coux, O., Tanaka, K., and Goldberg, A. L. (1996) *Annual Review of Biochemistry* 65, 801-847
6. Groll, M., Ditzel, L., Loewe, J., Stock, D., Bochtler, M., Bartunik, H. D., and Huber, R. (1997) *Nature* 386, 463-471
7. Baumeister, W., Walz, J., Zuhl, F., and Seemuller, E. (1998) *Cell* 92, 367-380
8. Kloetzel, P.-M., and Ossendorp, F. (2004) *Current Opinion in Immunology* 16, 76-81
9. Kloetzel, P. M. (2001) *Nat. Rev. Mol. Cell Biol.* 2, 179-187
10. Serwold T., Gonzalez F., Kim J., Jacob R., Shastri N. (2002) *Nature* 419, 480-483
11. Seifert, U., Maranon, C., Shmueli, A., Desoutter, J.-F., Wesoloski, L., Janek, K., Henklein, P., Diescher, S., Andrieu, M., de la Salle, H., Weinschenk, T., Schild, H., Laderach, D., Galy, A., Haas, G., Kloetzel, P.-M., Reiss, Y., and Hosmalin, A. (2003) *Nature Immunology* 4, 375-379

12. Golab, J., Bauer Thomas, M., Daniel, V., and Naujokat, C. (2004) *Clinica chimica acta; Int. J. Clin. Chem.* 340, 27-40
13. An, B., Goldfarb, R. H., Siman, R., and Dou, Q. P. (1998) *Cell Death and Differentiation* 5, 1062-1075
14. Orlowski, R. Z., Small, G. W., and Shi, Y. Y. (2002) *J. Biol. Chem.* 277, 27864-27871
15. Orlowski, R. Z., Eswara, J. R., Lafond-Walker, A., Grever, M. R., Orlowski, M., and Dang, C. V. (1998) *Cancer Research* 58, 4342-4348
16. Kisselev, A. F., and Goldberg, A. L. (2001) *Chemistry & Biology* 8, 739-758
17. Groll M., and Huber R. (2004) *Biochim. Biophys. Acta* 1695, 33-44.
18. Cusack Jr., J. C., Liu, R., Houston, M., Abendroth, K., Elliott, P. J., Adams, J., and Baldwin Jr, A. S. (2001) *Cancer Research* 61, 3535-3540
19. Orlowski, R. Z., Stinchcombe, T. E., Mitchell, B. S., Shea, T. C, Baldwin, A. S., Stahl, S., Adams, J., Esseltine, D.-L., Elliott, P. J., Pien, C. S., Guerciolini, R., Anderson, J. K., Depcik-Smith, N. D., Bhagat, R., Lehman, M. J., Novick, S. C., O'Connor, O. A., and Soignet, S. L. (2002) *J. Clinical Oncology* 20, 4420-4427
20. Paramore, A., and Frantz, S. (2003) *Nat. Rev. Drug. Discov.* 2, 611-612
21. Myung, J., Kim, K. B., and Crews, C. M. (2001) *Medicinal Research Reviews* 21, 245-273
22. Schmidt, B. (2003) *Chem Bio Chem* 4, 366-378
23. John, V., Beck, J. P., Bienkowski, M. J., Sinha, S., and Heinrikson, R. L. (2003) *J. Med. Chem.* 46, 4625-4630
24. Lesslie, A. G. (1994) *MRC Laboratory of Molecular Biology*, Cambrige, UK
25. Brunger, A. (1992) *Yale University Press*, New Haven.
26. Turk, D. (1992) *Thesis*, Technische Universitaet Muenchen
27. Engh, R., and Huber, R. (1991) *Acta Cryst.* A47, 392-400
28. Schmidt, B., Ehlert, D. K., and Braun, H. A. (2004) *Tetrahedron Lett.* 45, 1751-1753
29. Guzmen, M. L., Swiderski, C. F., Howard, D. S., Grimes, B. A., Rossi, R. M., Szilvassy, S. J., and Jordan, C. T. (2002) *Proc. Natl. Acad. Sci. USA* 99, 16220-5
30. Groll, M., Nazif, T., Huber, R., and Bogyo, M. (2002) *Chem. Biol.* 9, 655-62
31. Ling, Y. H., Liebes, L., Ng, B., Buckley, M., Elliott, P. J., Adams, J., Jiang, J. D., Muggia, F. M., and Perez-Soler, R. (2002) *Mol. Cancer Ther.* 1, 841-849
32. Meiners, S., Heyken, D., Wellej, A., Ludwig, A., Stangl, K., Kloetzel, P.-M., and Krüger, E. (2003) *J. Biol. Chem.* 278, 21517-25
33. Adams, J. (2004) *Nat. Rev. Cancer* 4, 349-360
34. Kisselev, A. F., and Goldberg, A. L. (2001) *Chem. Biol.* 8, 739-58
35. Traenker, E. B., Wilk. S., and Baeuerle, P. A. (1994) *EMBO J.* 13, 5433-41
36. Stoklosa, T., Golab, J., Wojcik, C., Wlodarski, P., Jalili, A., Januszko, P., Giermasz, A., Wilczynski, G. M., Pleban, E., Marczak, M., Wilk, S., and Jakobisiak, M. (2004) *Apoptosis* 9, 193-204
37. Hideshima, T., Richardson, P., Chauhan, D., Palombella, V. J., Elliott, P. J., Adams, J., and Anderson, K. C. (2001) *Cancer Res.* 61, 3071-3076
38. Garcia-Echeverria, C., Imbach, P., France, D., Fürst, P., Lang, M., Noorani, A. M., Scholz, D., Zimmermann, J., and Furet, P. (2001) *Bioorg Med Chem Lett.* 11, 1317-1319.
39. Prösch, S. et al. (2003) *Antiviral Therapy* 8:555-67.
40. Lou, H. et al. (2003) *Am J Pathol.* 163:381-85).
41. Golab, J. et al. (2004) *Clin. Chim. Acta* 340:27-40.

The invention claimed is:

1. A compound having the formula

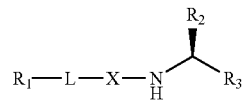

wherein
$R_1$ is Boc, Z, Ac or H,
Z is benzyloxycarbonyl,
L is Leu,
X is Leu or Asp(OR$_4$),
$R_2$ is $CH_2$—$CH(CH_3)_2$,
$R_3$ is $CH_2$—OH, CH=O, CH(OH)—C≡C-phenyl, CH(OH)—C(O)—NH—$R_5$ or C(O)—C(O)—NH—$R_5$,
$R_4$ is t-butyl, benzyl or H, and
$R_5$ is benzyl, 3-picolyl or phenyl,
with the exception of a compound wherein X is Leu and $R_3$ is CH=O,
and with the exception of a compound wherein X is Leu, $R_1$ is Ac and $R_3$ is $CH_2$—OH,
and pharmaceutically acceptable salts thereof.

2. The compound according to claim 1, wherein
$R_1$ is Boc or Z,
L is Leu,
X is Asp(OR$_4$),
$R_2$ is $CH_2$—$CH(CH_3)_2$,
$R_3$ is $CH_2$—OH, and
$R_4$ is t-butyl.

3. The compound according to claim 1, wherein
$R_1$ is Boc, Z or Ac,
L is Leu,
X is Asp(OR$_4$),
$R_2$ is $CH_2$—$CH(CH_3)_2$,
$R_3$ is CH=O, and
$R_4$ is t-butyl or benzyl.

4. The compound according to claim 1, wherein
$R_1$ is Z,
L is Leu,
X is Leu,
$R_2$ is $CH_2$—$CH(CH_3)_2$,
$R_3$ is C(O)—C(O)—NH—$R_5$, and
$R_5$ is benzyl, 3-picolyl or phenyl.

5. The compound according to claim 1, wherein
$R_1$ is Z,
L is Leu,
X is Leu,
$R_2$ is $CH_2$—$CH(CH_3)_2$,
$R_3$ is CH(OH)—C(O)—NH—$R_5$, and
$R_5$ is phenyl.

6. The compound according to claim 1, wherein
$R_1$ is Z,
L is Leu,
X is Leu,
$R_2$ is $CH_2$—$CH(CH_3)_2$, and
$R_3$ is CH(OH)—C≡C-phenyl.

7. A pharmaceutical composition, comprising a compound, and/or its salts, of claim 1, together with a pharmaceutically acceptable carrier and/or excipient.

8. The pharmaceutical composition according to claim 7, characterized in that the compound is present in an amount that effectively inhibits the proteasome-function in a cell or a mammal.

9. A method for inducing apoptosis in cells wherein said method comprises the use of a compound, and/or its salts, of claim 1.

10. A method for inhibiting the proteolytic activity of 20S proteasome, 26S proteasome, and immunoproteasome wherein said method comprises the use of a compound, and/or its salts, of claim 1.

11. The method according to claim 10, wherein specifically the trypsin-like activity of the 20S proteasome and 26S proteasome is inhibited.

12. The method according to claim 10, wherein specifically the chymotrypsin-like activity of the 20S proteasome and 26S proteasome is inhibited.

13. The method according to claim 10, wherein simultaneously the chymotrypsin-like, trypsin-like and caspase-like activities of the 20S proteasome and 26S proteasome are inhibited.

14. The method according to claim 10 for an in vitro, in vivo and/or intracellular inhibition.

* * * * *

UNITED STATES PATENT AND TRADEMARK OFFICE
CERTIFICATE OF CORRECTION

PATENT NO.       : 8,835,392 B2
APPLICATION NO.  : 11/817628
DATED            : September 16, 2014
INVENTOR(S)      : Boris Schmidt et al.

Page 1 of 1

It is certified that error appears in the above-identified patent and that said Letters Patent is hereby corrected as shown below:

In the Specification

Column 12,
Line 51, "2J=11.0 Hz)," should read --$^{2}J = 11.0$ Hz),--.

Column 15,
Line 36, "$^{3}J = 1.0$ Hz)," should read --$^{3}J = 7.0$ Hz),--.

Column 16,
Line 13, "($C_{10}$-Leu-$C_{10}$" should read --(CO-Leu-$C_{10}$--.

Column 23,
Line 43, "b=300.1 ÅA," should read --b = 300.1 Å,--.

Column 23,
Line 43, "and (β = 113.1°." should read --and $β$ = 113.1°.--.

Column 24,
Line 14, "takes a (β-conformation" should read --takes a $β$-conformation--.

Signed and Sealed this
Fourteenth Day of April, 2015

Michelle K. Lee
*Director of the United States Patent and Trademark Office*